US009382561B2

(12) United States Patent
Boisart et al.

(10) Patent No.: US 9,382,561 B2
(45) Date of Patent: Jul. 5, 2016

(54) STRAINS AND METHOD FOR THE PRODUCTION OF METHIONINE

(75) Inventors: Cedric Boisart, Gerzat (FR); Gwenaelle Bestel-Corre, Clermont-Ferrand (FR); Guillaume Barbier, Davis, CA (US); Rainer Figge, LeCrest (FR)

(73) Assignee: METABOLIC EXPLORER, Saint Beauzire (FR)

( * ) Notice: Subject to any disclaimer, the term of this patent is extended or adjusted under 35 U.S.C. 154(b) by 0 days.

(21) Appl. No.: 13/519,526

(22) PCT Filed: Dec. 29, 2010

(86) PCT No.: PCT/EP2010/070858
§ 371 (c)(1),
(2), (4) Date: Jun. 27, 2012

(87) PCT Pub. No.: WO2011/080301
PCT Pub. Date: Jul. 7, 2011

(65) Prior Publication Data
US 2012/0288904 A1  Nov. 15, 2012

Related U.S. Application Data

(60) Provisional application No. 61/290,975, filed on Dec. 30, 2009.

(30) Foreign Application Priority Data

Dec. 30, 2009 (EP) .................................... 09306349

(51) Int. Cl.
| C12P 13/12 | (2006.01) |
| C12N 1/20 | (2006.01) |
| C12N 1/00 | (2006.01) |
| C07H 21/04 | (2006.01) |
| C12N 9/10 | (2006.01) |
| C12N 9/88 | (2006.01) |
| C12N 15/52 | (2006.01) |

(52) U.S. Cl.
CPC .............. *C12P 13/12* (2013.01); *C12N 9/1014* (2013.01); *C12N 9/88* (2013.01); *C12N 15/52* (2013.01); *Y02P 20/52* (2015.11)

(58) Field of Classification Search
CPC ............ C12P 13/12; C12P 11/00; C12P 7/04; C12Q 1/6809; C12Q 1/689; C12Q 1/00; C12Q 1/48; C12N 15/52; C12N 9/1029; C12N 15/01; C12N 9/1085; C12N 15/8253; C12N 2500/32
See application file for complete search history.

(56) References Cited

U.S. PATENT DOCUMENTS

2008/0311632 A1* 12/2008 Figge et al. .................... 435/113

FOREIGN PATENT DOCUMENTS

| JP | 2000-157267 A | 6/2000 |
| WO | 02/097086 A1 | 12/2002 |
| WO | 2004076659 A2 | 9/2004 |
| WO | 2004081166 A2 | 9/2004 |
| WO | 2005/111202 A1 | 11/2005 |
| WO | 2007/020295 A2 | 2/2007 |
| WO | 2007077041 A1 | 7/2007 |
| WO | 2008/013432 A1 | 1/2008 |
| WO | 2008/101857 A2 | 8/2008 |
| WO | WO 2008/111708 i * | 9/2008 |
| WO | 2009/043372 A1 | 4/2009 |
| WO | 2009/043803 A2 | 4/2009 |
| WO | 2010/020290 A1 | 2/2010 |
| WO | 2011/080301 A2 | 7/2011 |

OTHER PUBLICATIONS

Datsenko et al., "One-Step Inactivation of Chromosomal Genes in *Escherichia coli* K-12 Using PCR Products," PNAS, vol. 97, No. 12, pp. 6640-6645, (Jun. 6, 2000).
Goss et al., "Molecular Characterization of the TDC Operon of *Escherichia coli* K-12," Journal of Bacteriology, vol. 170, No. 11, pp. 5352-5359 (Nov. 1988).
Komatsubara et al., "Threonine Degradation by Serratia Marcescens," Journal of Bacteriology, vol. 135, No. 2, pp. 318-323 (Aug. 1978).
Lee et al., "Systems Metabolic Engineering of *Escherichia coli* for L-Threonine Production," Molecular Systems Biology, vol. 3, Article 149, pp. 1-8 (2007).
Liebl et al., "Requirement of Chelating Compounds for the Growth of *Corynebacterium glutamicum* in Synthetic Media," Appl. Microbiol Biotechnol, vol. 32, pp. 205-210 (1989).
Liu et al., "Gene Cloning, Biochemical Characterization and Physiological Role of a Thermostable Low-Specificity L-Threonine Aldolase From *Escherichia coli*," Eur. J. Biochem, vol. 255, pp. 220-226 (1998).
Marcus et al., "Identity and Some Properties of the L-Threinine Aldolase Activity Manifested by Pure 2-Amino-3-Ketobutyrate Ligase of *Escherichia coli*," Biochimica et Biophysica Acta, vol. 1164, pp. 299-304, (1993).
Martinez-Force et al., "Amino Acid Overproduction and Catabolic Pathway Regulation in *Saccharomyces cerevisiae*, "Biotechnol. Prog., vol. 10, pp. 372-376, (1994).
Mukherjee et al., "Purification, Properties, and N-Terminal Amino Acid Sequence of Homogeneous *Escherichia coli* 2-Amino-3-Ketobutyrate COA Ligase, A Pyridoxal Phosphat-edependent Enzyme," The Journal of Biological Chemistry, vol. 262, No. 30, pp. 14441-14447, (Oct. 25, 1987).
Plamann et al., "Characterization of the *Escherichia coli* Gene for Serine Hydroxymethyltransferase," Gene, vol. 22, pp. 9-18, (1983).
Ramakrishnan et al., "Regulatory Mechanisms in the Biosynthesis of Isoleucine and Valine, III. Map Order of the Structural Genes and Operator Genes," Journal of Bacteriology, vol. 89, No. 3, pp. 661-664, (Mar. 1965)

(Continued)

*Primary Examiner* — Iqbal H Chowdhury
(74) *Attorney, Agent, or Firm* — Birch, Stewart, Kolasch & Birch, LLP

(57) ABSTRACT

The present invention relates to a method for the production of methionine using modified strains with attenuated transformation of threonine. This can be achieved by reducing threonine transformation into glycine, and/or by reducing its transformation to α-ketobutyrate. The invention also concerns the modified strains with attenuated transformation of threonine.

15 Claims, 1 Drawing Sheet

(56) References Cited

OTHER PUBLICATIONS

Riedel et al., "Characterization of the Phosphoenolpyruvate Carboxykinase Gene From *Corynebacterium glutamicum* and Significance of the Enzyme for Growth and Amino Acid Production," J. Mol. Microbiol. Biotechnol. vol. 3, No. 4, pp. 573-583 (2001).

Saunderson, "Comparative metabolism of L-Methionine, DL-Methionine and DL-2-Hydroxy 4-Methylthiobutanoic Acid By Broiler Chicks," British Journal of Nutrition, vol. 54, pp. 621-633, (1985).

Scarsdale et al., "Crystal Structure As 2.4 A Resolution of *E. coli* Serine Hydroxymethyltransferase in Complex With Glycone Substrate and 5-Formyl Tetrahydrofolate," J. Mol. Biol. vol. 296, pp. 155-168 (2000).

Schirch et al., "Serine Transhydroxymethylase—Identification As the Threonine and Allothreonine Aldolases," The Journal of Biological Chemistry, vol. 243, No. 21, pp. 5651-5655, (Nov. 10, 1968).

Schirch, "Serine Hydorxymethyltransferase," Advances in Enzymology and Related Area of Molecular Biology, pp. 83-112, (1982).

Schirch et al.,"Serine Hydroxymethyltransferase From *Escherichia coli*: Purification and Properties," Journal of Bacteriology, vol. 163, No. 1, pp. 1-7, (Jul. 1985).

Schirch et al., "Serine Hydroxymethyltransferase Revisited," Current Opinion in Chemical Biology, vol. 9, pp. 482-487, (2005).

Simic et al., "Identification of GLY4 (Encoding Serine Hydroxymethyltransferase) and Its Use Together With The Exporter Thre To Increase L-Threonine Accumulation by *Corynebacterium glutamicum*," Applied and Environmental Microbiology, vol. 68, No. 7, pp. 3321-3327, (Jul. 2002).

Su et al., "L-Serine Degradation in *Escherichia coli* K-12: Cloning and Sequencing of the sdaA Gene," Journal of Bacteriology, vol. 171, No. 9, pp. 5095-5102 (Sep. 1989).

Fujio et al., Novelty-"Microorganism Having a Inactivation or Deletion of 3 or More Genes Participating in Decomposition of Amino Acids or Nucleic Acids Are New," Database WPI Week 200316, XP-002603247 (2003).

Pascarella et al., "The Structure of Serine Hydroxymethyltransferase As Modeled by Homology and Validated by Site-Directed Mutagenesis," Protein Science, vol. 7, pp. 1976-1982, (1998).

Figge, "Methionine Biosynthesis in *Escherichia coli* and *Corynebacterium glutamicum*," Microbiol Monogr, (5), pp. 163-193, (2007).

Anderson, "Growth Requirements of Virus-Resistant Mutants of *Escherichia coli* Strain "B"," Proceeding from the National Academy of Sciences, vol. 32, pp. 120-128 (1946).

Angelaccio et al., "Serine Hydroxymethyltransferase: Origin of Substrate Specificity," Biochemistry, vol. 31, pp. 155-162, (1992).

Boylan et al., "L-Threonine Dehydrogenase," The Journal of Biological Chemistry, vol. 256, No. 4, pp. 1809-1815 (Feb. 25, 1981).

Schaefer et al., "Automated Sampling Device for Monitoring Intracellular Metabolite Dynamics," Analytical Biochemistry, vol. 270, pp. 88-96 (1999).

Carrier et al. "Library of Synthetic 5' Secondary Structures to Manipulate MRNA Stability in *Escherichia coli*" Biotechnol. Prog (1999) vol. 15, 58-64.

Su et al. "A Novel L-Serine Deaminase Activity in *Escherichia coli* K-12", Journal of Bacteriology (1991) 2473-2480.

Vivoli et al "Role of a Conserved Active Site Cation-π Interaction in *Escherichia coli* Serine Hydroxymethyltransferase", Biochemistry (2009) vol. 48, 12034-12046.

Kubota "Improved Production of L-Serine by Mutants of *Corynebacterium glycinophilum* With Less Serine Dehydratase Activity", Agric. Biol. Chem (1985) 49(1) 7-12. XP-002287205.

Gomes et al. "Production of L-Methionine by Submerged Fermentation: A Review", Enzyme and Mirobial Technology (2005) vol. 37, 3-18.

Marcus et al. "Threonine Formation via the Coupled Activity of 2-Amino-3-Ketobutyrate Coenzyme a Lyase and Threonine Dehydrogenase" Journal of Bacteriology (1993) 6505-6511. XP-002603248.

International Search Report of PCT/EP2010/070858 Mailed Feb. 22, 2012.

European Search Report of EP 09 30 6349 Dated Oct. 7, 2010.

Plamann et al., "Complete nucleotide sequence of the *E. coli* glyA gene" Nucleic Acids Research. (1983) vol. 11, No. 7: 2065-2075.

Su et al., "Use of gene fusions of the structural gene sdaA to purify L-serine deaminase from *Escherichia coli* K-12" Eur. J. Biochem. (1993), vol. 211: 521-527.

* cited by examiner

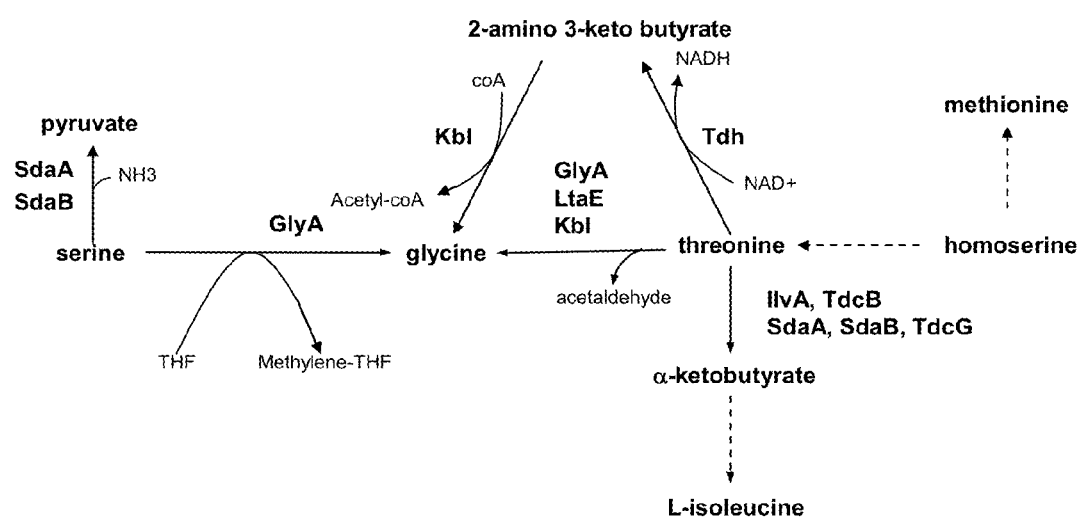

SEQUENCE LISTING

<160> NUMBER OF SEQ ID NOS: 22

<210> SEQ ID NO 1
<211> LENGTH: 101
<212> TYPE: DNA
<213> ORGANISM: Artificial Sequence
<220> FEATURE:
<223> OTHER INFORMATION: Oligonucleotide DltaE F

<400> SEQUENCE: 1
ggacatgcca tgattgattt acgcagtgat accgttaccc aaccaagccg cgccatgctc    60
gaagcgatga tggccgcccc atgtaggctg gagctgcttc g                        101

<210> SEQ ID NO 2
<211> LENGTH: 100
<212> TYPE: DNA
<213> ORGANISM: Artificial Sequence
<220> FEATURE:
<223> OTHER INFORMATION: Oligonucleotide DltaE R

<400> SEQUENCE: 2
gcgcaccaga tgctgaccaa tgtagccact ggcaccgaga actaaaatgc gttgcagcac    60
gtctctctcc ttaacgcgcc catatgaata tcctccttag                          100

<210> SEQ ID NO 3
<211> LENGTH: 21
<212> TYPE: DNA
<213> ORGANISM: Artificial Sequence
<220> FEATURE:
<223> OTHER INFORMATION: Oligonucleotide ltaE F

<400> SEQUENCE: 3
gccacctggc gctcctgagc g                                              21

<210> SEQ ID NO 4
<211> LENGTH: 21
<212> TYPE: DNA
<213> ORGANISM: Artificial Sequence
<220> FEATURE:
<223> OTHER INFORMATION: Oligonucleotide ltaE R

<400> SEQUENCE: 4
gctgcacaca atcatcagcg g                                              21

<210> SEQ ID NO 5
<211> LENGTH: 100
<212> TYPE: DNA
<213> ORGANISM: Artificial Sequence
<220> FEATURE:
<223> OTHER INFORMATION: Oligonucleotide Dtdh F

<400> SEQUENCE: 5
gaaagcgtta tccaaactga aagcggaaga gggcatctgg atgaccgacg ttcctgtacc    60
ggaactcggg cataacgatc catatgaata tcctccttag                          100

<210> SEQ ID NO 6
<211> LENGTH: 104
<212> TYPE: DNA
<213> ORGANISM: Artificial Sequence
<220> FEATURE:
<223> OTHER INFORMATION: Oligonucleotide Dtdh R

<400> SEQUENCE: 6
cccagctcag aataactttc ccggactggc ccgaacgcat agcgtcaaag cccttctgga    60
aatcatcgat agagaaacga tgggtgtagg ctggagctgc ttcg 104

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide tdh F

<400> SEQUENCE: 7
gggtagagag ataatgagag cagc 24

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide tdh R

<400> SEQUENCE: 8
gcccagccaa aactgtacag 20

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide

<400> SEQUENCE: 9
ctggctggtg taggcgaccc 20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide

<400> SEQUENCE: 10
ccattcccca gccgatcagc 20

<210> SEQ ID NO 11
<211> LENGTH: 23
<212> TYPE: DNA
<213> ORGANISM: Artificial Sequence
<220> FEATURE:
<223> OTHER INFORMATION: Oligonucleotide

<400> SEQUENCE: 11
ggaagaacag cgtgctaatg gcg 23

<210> SEQ ID NO 12
<211> LENGTH: 25
<212> TYPE: DNA
<213> ORGANISM: Artificial Sequence
<220> FEATURE:
<223> OTHER INFORMATION: Oligonucleotide

<400> SEQUENCE: 12
cggctcttca tcttcatcat ctgcg 25

<210> SEQ ID NO 13
<211> LENGTH: 99
<212> TYPE: DNA

```
<213> ORGANISM: Artificial Sequence
<220> FEATURE:
<223> OTHER INFORMATION: Oligonucleotide

<400> SEQUENCE: 13
atgttaaagc gtgaaatgaa cattgccgat tatgatgccg aactgtggca ggctatggag     60
caggaaaaag tacgtcaggt gtaggctgga gctgcttcg                           99

<210> SEQ ID NO 14
<211> LENGTH: 99
<212> TYPE: DNA
<213> ORGANISM: Artificial Sequence
<220> FEATURE:
<223> OTHER INFORMATION: Oligonucleotide

<400> SEQUENCE: 14
gcacagatgt cgagaacttt acctttgatg cgctcgataa cggcttcatc attgatgctg     60
tccagcacat cacacatccc atatgaatat cctccttag                           99

<210> SEQ ID NO 15
<211> LENGTH: 23
<212> TYPE: DNA
<213> ORGANISM: Artificial Sequence
<220> FEATURE:
<223> OTHER INFORMATION: Oligonucleotide

<400> SEQUENCE: 15
cgccgttgtc caacaggacc gcc                                            23

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide

<400> SEQUENCE: 16
cctgatgcgc tacacttatc                                                20

<210> SEQ ID NO 17
<211> LENGTH: 45
<212> TYPE: DNA
<213> ORGANISM: Artificial Sequence
<220> FEATURE:
<223> OTHER INFORMATION: Oligonucleotide

<400> SEQUENCE: 17
atctagtaag cttagtgaat tcgttacgac agatttgatg gcgcg                    45

<210> SEQ ID NO 18
<211> LENGTH: 39
<212> TYPE: DNA
<213> ORGANISM: Artificial Sequence
<220> FEATURE:
<223> OTHER INFORMATION: Oligonucleotide

<400> SEQUENCE: 18
tcatcggatc catcaagctt gaaagaatgt gatgaagtg                           39

<210> SEQ ID NO 19
<211> LENGTH: 49
<212> TYPE: DNA
<213> ORGANISM: Artificial Sequence
<220> FEATURE:
<223> OTHER INFORMATION: Oligonucleotide
```

<400> SEQUENCE: 19

```
cctttcgcca ggatcaggcc tcctttcgga cccgccaggg ttttgtgag         49
```

<210> SEQ ID NO 20
<211> LENGTH: 49
<212> TYPE: DNA
<213> ORGANISM: Artificial Sequence
<220> FEATURE:
<223> OTHER INFORMATION: Oligonucleotide

<400> SEQUENCE: 20

```
ctcacaaaac cctggcgggt ccgaaaggag gcctgatcct ggcgaaagg         49
```

<210> SEQ ID NO 21
<211> LENGTH: 1365
<212> TYPE: DNA
<213> ORGANISM: Escherichia coli
<220> FEATURE:
<221> NAME/KEY: misc_feature
<222> LOCATION: (1)..(1365)
<223> OTHER INFORMATION: sdaA gene

<400> SEQUENCE: 21

```
gtgattagtc tattcgacat gtttaaggtg gggattggtc cctcatcttc ccataccgta    60
gggcctatga aggcaggtaa acagttcgtc gatgatctgg tcgaaaaagg cttactggat   120
agcgttactc gcgttgccgt ggacgtttat ggttcactgt cgctgacggg taaaggccac   180
cacaccgata tcgccattat tatgggtctt gcaggtaacg aacctgccac cgtggatatc   240
gacagtattc ccggttttat tcgcgacgta gaagagcgcg aacgtctgct gctggcacag   300
ggacggcatg aagtggattt cccgcgcgac aacgggatgc gttttcataa cggcaacctg   360
ccgctgcatg aaaacggtat gcaaatccac gcctataacg cgatgaagt cgtctacagc   420
aaaacttatt attccatcgg cggcggtttt atcgtcgatg aagaacactt tggtcaggat   480
gctgccaacg aagtaagcgt gccgtatccg ttcaaatctg ccaccgaact gctcgcgtac   540
tgtaatgaaa ccggctattc gctgtctggt ctcgctatgc agaacgaact ggcgctgcac   600
agcaagaaag agatcgacga gtatttcgcg catgtctggc aaaccatgca ggcatgtatc   660
gatcgcggga tgaacaccga aggtgtactg ccaggcccgc tgcgcgtgcc acgtcgtgcg   720
tctgccctgc gccggatgct ggtttccagc gataaactgt ctaacgatcc gatgaatgtc   780
attgactggg taaacatgtt tgcgctggca gttaacgaag aaaacgccgc cggtggtcgt   840
gtggtaactg cgccaaccaa cggtgcctgc ggtatcgttc cggcagtgct ggcttactat   900
gaccacttta ttgaatcggt cagcccggac atctataccc gttactttat ggcagcgggc   960
gcgattggtg cattgtataa aatgaacgcc tctatttccg gtgcggaagt tggttgccag  1020
ggcgaagtgg gtgttgcctg ttcaatggct gctgcgggtc ttgcagaact gctgggcggt  1080
agcccggaac aggtttgcgt ggcggcgaa attggcatgg aacacaacct tggtttaacc  1140
tgcgacccgg ttgcagggca ggttcaggtg ccgtgcattg agcgtaatgc cattgcctct  1200
gtgaaggcga ttaacgccgc gcggatggct ctgcgccgca ccagtgcacc gcgcgtctcg  1260
ctggataagg tcatcgaaac gatgtacgaa accggtaagg acatgaacgc caaataccgc  1320
gaaacctcac gcggtggtct ggcaatcaaa gtccagtgtg actaa             1365
```

<210> SEQ ID NO 22
<211> LENGTH: 417
<212> TYPE: PRT

<213> ORGANISM: Escherichia coli
<220> FEATURE:
<221> NAME/KEY: MISC_FEATURE
<222> LOCATION: (1)..(417)
<223> OTHER INFORMATION: GlyA protein

<400> SEQUENCE: 22

```
Met Leu Lys Arg Glu Met Asn Ile Ala Asp Tyr Asp Ala Glu Leu Trp
1               5                   10                  15

Gln Ala Met Glu Gln Glu Lys Val Arg Gln Glu Glu His Ile Glu Leu
            20                  25                  30

Ile Ala Ser Glu Asn Tyr Thr Ser Pro Arg Val Met Gln Ala Gln Gly
        35                  40                  45

Ser Gln Leu Thr Asn Lys Tyr Ala Glu Gly Tyr Pro Gly Lys Arg Tyr
    50                  55                  60

Tyr Gly Gly Cys Glu Tyr Val Asp Ile Val Glu Gln Leu Ala Ile Asp
65                  70                  75                  80

Arg Ala Lys Glu Leu Phe Gly Ala Asp Tyr Ala Asn Val Gln Pro His
                85                  90                  95

Ser Gly Ser Gln Ala Asn Phe Ala Val Tyr Thr Ala Leu Leu Glu Pro
            100                 105                 110

Gly Asp Thr Val Leu Gly Met Asn Leu Ala His Gly Gly His Leu Thr
        115                 120                 125

His Gly Ser Pro Val Asn Phe Ser Gly Lys Leu Tyr Asn Ile Val Pro
    130                 135                 140

Tyr Gly Ile Asp Ala Thr Gly His Ile Asp Tyr Ala Asp Leu Glu Lys
145                 150                 155                 160

Gln Ala Lys Glu His Lys Pro Lys Met Ile Ile Gly Gly Phe Ser Ala
                165                 170                 175

Tyr Ser Gly Val Val Asp Trp Ala Lys Met Arg Glu Ile Ala Asp Ser
            180                 185                 190

Ile Gly Ala Tyr Leu Phe Val Asp Met Ala His Val Ala Gly Leu Val
        195                 200                 205

Ala Ala Gly Val Tyr Pro Asn Pro Val Pro His Ala His Val Val Thr
    210                 215                 220

Thr Thr Thr His Lys Thr Leu Ala Gly Pro Arg Gly Gly Leu Ile Leu
225                 230                 235                 240

Ala Lys Gly Gly Ser Glu Glu Leu Tyr Lys Lys Leu Asn Ser Ala Val
                245                 250                 255

Phe Pro Gly Gly Gln Gly Gly Pro Leu Met His Val Ile Ala Gly Lys
            260                 265                 270

Ala Val Ala Leu Lys Glu Ala Met Glu Pro Glu Phe Lys Thr Tyr Gln
        275                 280                 285

Gln Gln Val Ala Lys Asn Ala Lys Ala Met Val Glu Val Phe Leu Glu
    290                 295                 300

Arg Gly Tyr Lys Val Val Ser Gly Gly Thr Asp Asn His Leu Phe Leu
305                 310                 315                 320

Val Asp Leu Val Asp Lys Asn Leu Thr Gly Lys Glu Ala Asp Ala Ala
                325                 330                 335

Leu Gly Arg Ala Asn Ile Thr Val Asn Lys Asn Ser Val Pro Asn Asp
            340                 345                 350

Pro Lys Ser Pro Phe Val Thr Ser Gly Ile Arg Val Gly Thr Pro Ala
        355                 360                 365

Ile Thr Arg Arg Gly Phe Lys Glu Ala Glu Ala Lys Glu Leu Ala Gly
    370                 375                 380
```

```
Trp Met Cys Asp Val Leu Asp Ser Ile Asn Asp Glu Ala Val Ile Glu
385                 390                 395                 400

Arg Ile Lys Gly Lys Val Leu Asp Ile Cys Ala Arg Tyr Pro Val Tyr
                405                 410                 415

Ala
```

STRAINS AND METHOD FOR THE PRODUCTION OF METHIONINE

CROSS REFERENCE TO RELATED APPLICATIONS

This application is a §371 National Stage Application of PCT/EP2010/070858, filed Dec. 29, 2010, which claims priority to European Application No. 09306349.3, filed Dec. 30, 2009, and to U.S. Provisional Application No. 61/290,975, filed Dec. 30, 2009.

BACKGROUND OF THE INVENTION

1. Field of the Invention

The present invention relates to a method for the production of methionine using modified strains with attenuated transformation of threonine. This can be achieved by reducing threonine degradation to glycine, and/or by reducing its transformation to α-ketobutyrate. The invention also concerns the modified strains with attenuated transformation of threonine.

2. Description of Related Art

Sulphur-containing compounds such as cysteine, homocysteine, methionine or S-adenosylmethionine are critical to cellular metabolism and are produced industrially to be used as food or feed additives and pharmaceuticals. In particular methionine, an essential amino acid, which cannot be synthesized by animals, plays an important role in many body functions. Aside from its role in protein biosynthesis, methionine is involved in transmethylation and in the bioavailability of selenium and zinc. Methionine is also directly used as a treatment for disorders like allergy and rheumatic fever. Nevertheless most of the methionine that is produced is added to animal feed.

With the decreased use of animal-derived proteins as a result of BSE and chicken flu, the demand for pure methionine has increased. Chemically D,L-methionine is commonly produced from acrolein, methyl mercaptan and hydrogen cyanide. Nevertheless the racemic mixture does not perform as well as pure L-methionine, as for example in chicken feed additives (Saunderson C. L., (1985) British Journal of Nutrition 54, 621-633). Pure L-methionine can be produced from racemic methionine e.g. through the acylase treatment of N-acetyl-D,L-methionine which increases production costs dramatically. The increasing demand for pure L-methionine coupled to environmental concerns render microbial production of methionine attractive.

Methionine biosynthesis depends on homoserine, cysteine and C1 unit productions. Homoserine is a derivative of aspartarte and provides the carbon skeleton for methionine. Homoserine can also be transformed into threonine, which in turn is the precursor of (i) isoleucine and which can also be transformed into glycine (ii). These two reactions consume threonine and draw more homoserine into the threonine pathway, thus reducing the flux into the methionine pathway.

(i) For the production of isoleucine, threonine is deaminated to a-ketobutyrate, a reaction catalysed by threonine deaminase or threonine dehydratase encoded by the genes ilvA (EC 4.3.1.19, Ramakrishnan et al., 1965, J Bacteriol, 89:661) and tdcB (EC 4.3.1.19, Goss et al., 1988, J Bacteriol, 170:5352), respectively. Serine deaminases encoded by sdaA (EC 4.3.1.17; Su et al. 1989, J Bacteriol, 171:5095; SEQ ID NO: 21) and sdaB (EC 4.3.1.17, Su and Newman, 1991, 173:2473) are also known to encode some threonine deaminase activity.

(ii) Two pathways for threonine glycine transformation are present in *E. coli:*

(A) Threonine can be transformed into glycine by two consecutive reactions catalyzed by threonine dehydrogenase (Tdh; E.C. 1.1.1.103) and 2-amino 3-keto butyrate-coA-lyase (Kbl; E.C. 2.3.1.29) (Boylan S. A. et al., 1981, Journal of Biological Chemistry, 256, 4, pp 1809-1815; Mukherjee J. J. et al., 1987, Journal of Biological Chemistry, 262, 30, pp 14441-14447). These reactions generate a molecule of acetyl-coA and NADH each. (Komatsubara S. et al., 1978, Journal of Bacteriology, 1981, 135, pp 318-323).

(B) Threonine can also be transformed into glycine directly via a retroaldol mechanism catalysed by threonine aldolase. This reaction generates an acetaldehyde and a glycine (Plamann M. D. et al., 1983, Gene, 22, 1, pp 9-18). Threonine aldolase activity carrying enzymes in *E. coli* are encoded by the following genes: ltaE (Liu J L et al., 1998, European Journal of Biochemistry, 255, 1, pp 220-226), kbl (Markus J. P. et al., 1993, Biochemica et Biophysica Acta, 1164, pp 299-304) and glyA (Schirch V. et al., 1968, Journal of Biological Chemistry, 243, pp 5561; Schirch V. et al., 1985, Journal of Bacteriology, 163, 1, pp 1-7).

LtaE is a low specific threonine aldolase which is thought to be involved in the degradation of threonine to form acetaldehyde and glycine (Liu J L et al., 1998, European Journal of Biochemistry, 255, 1, pp 220-226).

The primary activity of Kbl is 2-amino-3-ketobutyrate CoA ligase (E.C 2.3.1.29), which consists of the deacetylation of the 2-amino 3-ketobutyrate to form glycine and acetyl-coenzyme A (Mukherjee J.J. et al., 1987, Journal of Biological Chemistry, 262, 30pp 14441 - 14447). It has been shown to posses TAL activity, which makes it a versatile enzyme for threonine degradation (Markus J.P. et al., 1993, Biochemica et Biophysica Acta, 1164, pp 299-304).

The primary activity of GlyA (SEQ ID NO: 22) is serine hydroxymethyltransferase (SHMT) (E.C. 2.1.2.1). It catalyses the conversion of the amino acid serine and tetrahydrofolate (THF) into glycine and 5,10methylene-THF (for review: Schirch V. et al., 2005, Current opinion in Chemical biology, 9, pp 482-487). Among the other secondary activities catalyzed by GlyA (for review: Schirch L., 2006, Advances in enzymology and related areas of molecular biology, 53, pp 83-112), only threonine aldolase (TAL) seems to be physiologically relevant. GlyA was crystallized (Scarsdale et al., 2000, Journal of Molecular Biology, 296, pp 155-168) and studies have been done to elucidate the origin of the substrate specificity (Angelaccio S. et al., 1992, Biochemistry, 31, pp 155-162). Angelaccio et al. mutated all threonines in the vicinity of the active site to alanine, and noticed that mutation T226A increased the Km of threonine by a factor 1.8 and decreased TAL activity to levels inferior to their quantification limit, while not modifying the Km for THF nor the Km for serine. Nevertheless, the mutation has a strong impact on the SHMT activity, since the $k_{cat}$ for the SHMT reaction was decreased by a factor 32.

Strains for producing methionine being modified for an improved yield are now extensively disclosed in the art. It is now understood that the methionine biosynthesis pathway is particularly complex with genes involved in many other pathways. Therefore, enhancing or attenuating a gene susceptible to be beneficial to promote the synthesis of methionine at first sight may end into an opposite result. It is known that genes involved in threonine consumption are also known to be involved in C1 production.

The inhibition of the activity or the attenuation of the expression of proteins involved in threonine degradation are already disclosed in several works. Simic et al. (Simic et al, 2002, Applied and Environmental microbiology, 68(7), pp 3321-3327) disclose attenuation of aldole cleavage of threonine activity of the GlyA protein to enhance threonine production in *Corynebacterium glutamicum*. Martinez-Force et al. (Martinez-Force et al, 1994, Biotechnology Progress, 10(4), pp 372-376) disclose deletion of the ilv1 gene in *Saccharomyces cerevisiae* to enhance threonine production. Moreover, in this study, the authors show that there is no correlation between threonine and methionine accumulation and the decrease in threonine deaminase activity. Liu et al. (Liu et al, 1998, European Journal of Biochemistry, 255(1), pp 220-226) detailed the characterization of the LtaE enzyme from *Escherichia coli* and its role in the growth of cell. Finally, Lee et al. (Lee et al, 2007, Molecular Systems Biology, 3(149), pp 1-8) disclose deletion of tdh and mutation of ilvA genes to enhance threonine production.

All of these studies are exclusively oriented towards threonine production. It has never been considered in the prior art to prevent threonine consumption as a solution to improve methionine biosynthesis.

Despite the complexity of the methionine metabolic pathway, the inventors have found a method to increase methionine production by acting on the threonine transformation.

SUMMARY

The present invention concerns a method for the production of methionine, its precursors or derivatives in a fermentative process comprising the following steps:

culturing a modified microorganism in an appropriate culture medium comprising a source of carbon, a source of sulphur and a source of nitrogen, and recovering methionine and/or its derivatives from the culture medium, wherein the microorganism is modified in a way to reduce the transformation of threonine in other compounds than methionine.

In particular, the transformation of threonine into glycine or isoleucine is reduced.

The invention also concerns the microorganism modified for an improved methionine production in which the transformation of threonine in other compounds than methionine is reduced, in combination with other genetic modifications for the improvement of methionine production.

The production of glycine from threonine is reduced, particularly by reducing the activity of enzymes that transform threonine to glycine. In one particular embodiment, a mutant GlyA enzyme is expressed that has an attenuated threonine aldolase activity, while the serine hydroxymethyl transferase activity of said enzyme GlyA is maintained.

The production of isoleucine from threonine is reduced particularly by reducing the deamination and/or the dehydratation of threonine to alpha-ketobutyrate.

BRIEF DESCRIPTION OF THE DRAWING

FIG. 1 show the metabolic pathway involving pyruvate, threonine, isoleucine and methionine.

DETAILED DESCRIPTION OF A PREFERRED EMBODIMENT

The invention is related to a method for the production of methionine, its precursors or derivatives in a fermentative process comprising the following steps:

culturing a modified microorganism in an appropriate culture medium comprising a source of carbon, a source of sulphur and a source of nitrogen, and recovering methionine and/or its derivatives from the culture medium, wherein the microorganism is modified in a way to reduce transformation of threonine into other compounds than methionine.

According to the invention, precursors of methionine are defined as metabolites that are part of the methionine specific metabolic pathway or can be derived of these metabolites. Derivatives of methionine originate from methionine transforming and/or degrading pathways such as S-acyl methionine and N-acyl methionine. In particular these products are S-adenosyl-methionine (SAM) and N-acetylmethionine (NAM). Especially NAM is an easily recoverable methionine derivative that may be isolated and transformed into methionine by deacylation.

The phrase "recovering methionine from the culture medium" designates the action of recovering methionine and, possibly SAM and NAM and all other derivatives that may be useful.

The terms "fermentative process', 'culture' or 'fermentation" are used interchangeably to denote the growth of bacteria on an appropriate growth medium containing a simple carbon source, a source of sulphur and a source of nitrogen.

An "appropriate culture medium" is a medium appropriate for the culture and growth of the microorganism. Such media are well known in the art of fermentation of microorganisms, depending upon the microorganism to be cultured.

The term "microorganism" designates a bacterium, yeast or fungus. Preferentially, the microorganism is selected among *Enterobacteriaceae, Bacillaceae, Streptomycetaceae* and *Corynebacteriaceae*. More preferentially, the microorganism is a species of *Escherichia, Klebsiella, Pantoea, Salmonella* or *Corynebacterium*. Even more preferentially, the microorganism is either the species *Escherichia coli* or *Corynebacterium glutamicum*.

The term "modified microorganism" is a microorganism modified for an improved methionine production and denotes a microorganism that has been genetically modified with the goal to improve the production yield of methionine. According to the invention, "improved" or "improve" means that the amount of methionine produced by the microorganism, and particularly the methionine yield (ratio of gram/mol methionine produced per gram/mol carbon source), is higher in the modified microorganism compared to the corresponding unmodified microorganism. Usual modifications include introducing deletions of genes into microorganisms by transformation and recombination, gene replacements, and introduction of vectors for the expression of heterologous genes.

According to the invention, the modified microorganism used in this method comprises, on one hand, modifications for an improved methionine production and, on the other hand, modifications for a reduced production of other compounds than methionine from threonine in comparison with the unmodified microorganism.

The phrase "other compounds than methionine" designates in particular glycine and isoleucine.

Genes involved in methionine production in a microorganism are known in the art, and comprise genes involved in the methionine specific biosynthesis pathway as well as genes involved in precursor-providing pathways and genes involved in methionine consuming pathways.

Efficient production of methionine requires the optimisation of the methionine specific pathway and several precursor-providing pathways. Methionine producing strains have been described in patent applications WO 2005/111202, WO2007/077041 and WO2009/043803 and are incorporated as reference into this application.

A methionine producing strain that overexpresses homoserine succinyltransferase alleles with reduced feed-back sensitivity to its inhibitors SAM and methionine is described in patent application WO 2005/111202. This application describes also the combination of these alleles with a deletion of the methionine repressor MetJ (GenBank 1790373), responsible for the down-regulation of the methionine regulon as was suggested in patent application JP 2000/157267. In addition, combinations of the two modifications with the overexpression of aspartokinase/homoserine dehydrogenase are described in patent application WO 2005/111202.

The overexpression of the genes cysE, metH and metF has been suggested in WO 2007/077041.

For improving the production of methionine, the microorganism may exhibit:

an increased expression of at least one gene selected in the group consisting of:
- cysP which encodes a periplasmic sulphate binding protein, as described in WO2007/077041 and in WO2009/043803,
- cysU which encodes a component of sulphate ABC transporter, as described in WO2007/077041 and in WO2009/043803,
- cysW which encodes a membrane bound sulphate transport protein, as described in WO2007/077041 and in WO2009/043803,
- cysA which encodes a sulphate permease, as described in WO2007/077041 and in WO2009/043803,
- cysM which encodes an O-acetyl serine sulfhydralase, as described in WO2007/077041 and in WO2009/043803,
- cysI and cysJ encoded respectively the alpha and beta subunits of a sulfite reductase as described in WO2007/077041 and in WO2009/043803. Preferably cysI and cysJ are overexpressed together,
- cysH which encodes an adenylylsulfate reductase, as described in WO2007/077041 and in WO2009/043803,
- cysE which encodes a serine acyltransferase, as described in WO2007/077041,
- gcvT which encodes a tetrahydrofolate dependent aminomethyl transferase, as described in WO2007/077041 and in WO2009/043803,
- gcvH which is involved in glycine cleavage by encoding a carrier of aminoethyl group, as described in WO2007/077041 and in WO2009/043803,
- gcvP which encodes a glycine dehydrogenase, as described in WO2007/077041 and in WO2009/043803,
- lpd which encodes a lipoamide dehydrogenase, as described in WO2007/077041 and in WO2009/043803,
- serA which encodes a phosphoglycerate dehydrogenase, as described in WO2007/077041 and in WO2009/043803,
- serB which encodes a phosphoserine phosphatase, as described in WO2007/077041 and in WO2009/043803,
- serC which encodes a phosphoserine aminotransferase, as described in WO2007/077041 and in WO2009/043803,
- glyA which encodes a serine hydroxymethyltransferase, as described in WO2007/077041 and in WO2009/043803,
- metF which encodes a 5,10-methylenetetrahydrofolate reductase, as described in WO2007/077041,
- metA alleles which encode an homoserine succinyltransferases with reduced feed-back sensitivity to S-adenosylmethionine and/or methionine as described in WO2005/111202,
- thrA or thrA alleles which encode aspartokinases/homoserine dehydrogenase with reduced feed-back inhibition to threonine, as described in WO2009/043803 and WO2005/111202,
- metH which encodes a B12-dependent homocysteine-N-5-methyltetrahydrofolate transmethylase as described in WO2007/077041, and/or an inhibition of the expression of at least one of the following genes:
- pykA which encodes a pyruvate kinase, as described in WO2007/077041 and in WO2009/043803,
- pykF which encodes a pyruvate kinase, as described in WO2007/077041 and in WO2009/043803,
- purU which encodes a formyltetrahydrofolate deformylase, as described in WO2007/077041 and in WO2009/043803.

Microorganisms according to the present invention, may be further modified for increasing production of methionine by using an altered metB allele that uses preferentially or exclusively H2S for the production of homocysteine from O-succinyl-homoserine as described in the patent application WO2004/076659 that is herein incorporated by reference.

The person skilled in the art will know that other genes may require modifications to optimize methionine production. These genes have been identified in WO2007/077041 and in WO2007/020295.

All references to patents and patent applications related to methionine production cited above are incorporated herein by reference.

In a first aspect of the invention, the production of glycine from threonine is reduced by attenuating the activity of enzymes that transform threonine to glycine.

The terms "reduced', 'attenuated" are used interchangeably in the text and have similar meaning. In this text, the terms denote the partial or complete suppression of the activity of an enzyme or of the expression of a gene, which is then said to be 'reduced' or 'attenuated'.

Enzyme activity may be reduced by mutating the enzyme in its amino acid sequence, by reducing the translation of the enzyme from the corresponding RNA or by reducing expression of the corresponding gene. The man skilled in the art knows many methods for reducing translation. Enzyme expression may be reduced by elements stabilizing or destabilizing the corresponding messenger RNA (Carrier and Keasling (1998) Biotechnol. Prog. 15, 58-64) or the proteins (e.g. GST tags, Amersham Biosciences). Gene expression may be reduced partially or completely. This reduction of gene expression can be either an inhibition of the expression of the gene, a deletion of all or part of the promoter region necessary for the gene expression, a deletion in the coding region of the gene, or the exchange of the wild type promoter by a weaker natural or synthetic promoter. Preferentially, the attenuation of a gene is essentially the complete deletion of that gene, which can be replaced by a selection marker gene that facilitates the identification, isolation and purification of the strains.

In a first aspect of the invention, the production of glycine from threonine is reduced in the modified microorganism.

In a specific aspect, the activity of enzymes that transform threonine into glycine is reduced.

In a more specific embodiment of the invention, the expression of at least one of the following genes is attenuated in the modified microorganism: ltaE, kbl, glyA, tdh.

In another specific embodiment of the invention, the modified microorganism expresses a mutant GlyA enzyme that has an attenuated threonine aldolase (TAL) activity, while the serine hydroxymethyl transferase activity of said enzyme GlyA is maintained. More precisely, according to the invention, the GlyA enzyme may have at least one of the following amino acid changes in its polypeptidic sequence: T128S, T224S, T225S, T226S, T227S, T230S, R235K. The most preferred amino acid change is R235K.

In a particular embodiment of the invention, the endogenous gene glyA has been deleted from the microorganism.

In a second aspect of the invention, the microorganism is modified in a way that the production of isoleucine from threonine is reduced.

In particular, the transformation of isoleucine from threonine is reduced by reducing the deamination and/or the dehydratation of threonine to alpha-ketobutyrate.

In a particular embodiment of the invention, at least one of the following enzyme activities is attenuated: threonine deaminase, threonine dehydratase. In a more particular embodiment of the invention, at least one of the following genes is attenuated in the modified microorganism: ilvA, tdcB, sdaA, sdaB, tdcG.

According to the invention, the serine availability in the modified microorganism may be increased, additionally to the reduction of the production of glycine and/or isoleucine from threonine.

The phrase 'serine availability is increased' designates the fact that the internal pool of serine, available for metabolic pathways, is increased compared to an unmodified microorganism. Said increase is obtained by different means: increase of the internal production, decrease of the degradation, decrease of the transport toward the exterior, and all other ways known by the man skilled in the art.

Particularly, serine production may be increased in the microorganism by increasing the expression of at least one of the genes serA, serB, serC. Moreover, serine degradation may be decreased by attenuating the activity of at least one of the genes sdaA or sdaB, encoding enzymes with serine deaminase activity. In a preferred embodiment of the invention the sdaA gene has a thymidine nucleotide at the position 158 instead of a guanine.

In a more particular embodiment of the invention, the expression of glyA alleles with reduced threonine aldolase activity, as described above, may be increased.

In the description of the present invention, genes and proteins are identified using the denominations of the corresponding genes in *E. coli*. However, and unless specified otherwise, use of these denominations has a more general meaning according to the invention and covers all the corresponding genes and proteins in other organisms, more particularly microorganisms.

Using the references given in GenBank for known genes, those skilled in the art are able to determine the equivalent genes in other organisms, bacterial strains, yeasts, fungi, mammals, plants, etc. This routine work is advantageously done using consensus sequences that can be determined by carrying out sequence alignments with genes derived from other microorganisms, and designing degenerate probes to clone the corresponding gene in another organism. These routine methods of molecular biology are well known to those skilled in the art, and are claimed, for example, in Sambrook et al. (1989 Molecular Cloning: a Laboratory Manual. $2^{nd}$ ed. Cold Spring Harbor Lab., Cold Spring Harbor, New York.).

PFAM (protein families database of alignments and hidden Markov models, that can be used on the Wellcome Trust Sanger Institute website, represents a large collection of protein sequence alignments. Each PFAM makes it possible to visualize multiple alignments, see protein domains, evaluate distribution among organisms, gain access to other databases, and visualize known protein structures.

COGs (clusters of orthologous groups of proteins), that can be used on the National Center for Biotechnology Information website; are obtained by comparing protein sequences from fully sequenced genomes representing major phylogenic lines. Each COG is defined from at least three lines, which permits the identification of former conserved domains.

The means of identifying homologous sequences and their percentage homologies are well known to those skilled in the art, and include in particular the BLAST programs, which can be used from the National Center for Biotechnology Information website with the default parameters indicated on that website. The sequences obtained can then be exploited (e.g., aligned) using, for example, the programs CLUSTALW, that can be used on the European Bioinformatics Institute website or MULTALIN, that can be used on the MultAlin website with the default parameters indicated on those websites.

The method for the production of methionine, its precursors or derivatives in a fermentative process, is well known by the man skilled in the art. Different factors of the fermentative process can be modulated for the optimization of the process, such as the choice of the sulphur source, of the carbon source, and of the nitrogen source.

In a preferred aspect of the invention, the sulphur source used for the fermentative production of L-methionine, added in the culture medium, is sulfate, thiosulfate, hydrogen sulfide, dithionate, dithionite, sulfite, methylmercaptan, dimethyldisulfide and other methyl capped sulfides or a combination of the different sources.

More preferentially, the sulphur source in the culture medium is sulfate or thiosulfate, or a mixture thereof.

The term 'carbon source' according to the present invention denotes any source of carbon that can be used by those skilled in the art to support the normal growth of a microorganism, which can be hexoses (such as glucose, galactose or lactose), pentoses, monosaccharides, disaccharides (such as sucrose, cellobiose or maltose), oligosaccharides, molasses, starch or its derivatives, hemicelluloses, glycerol and combinations thereof. An especially preferred carbon source is glucose. Another preferred carbon source is sucrose.

In a particular embodiment of the invention, the carbon source is derived from renewable feed-stock. Renewable feed-stock is defined as raw material required for certain industrial processes that can be regenerated within a brief delay and in sufficient amount to permit its transformation into the desired product.

The term nitrogen source corresponds to either an ammonium salt or ammoniac gas.

The nitrogen source is supplied in the form of ammonium or ammoniac.

The fermentation is generally conducted in fermenters with an appropriate culture medium adapted to the microorganism being used, containing at least one simple carbon source, and if necessary co-substrates for the production of metabolites.

Those skilled in the art are able to define the culture conditions for the microorganisms according to the invention. In particular the bacteria are fermented at a temperature between 20° C. and 55° C., preferentially between 25° C. and 40° C., and more specifically about 30° C. for *C. glutamicum* and about 37° C. for *E. coli*.

As an example of known culture medium for *E. coli*, the culture medium can be of identical or similar composition to an M9 medium (Anderson, 1946, *Proc. Natl. Acad. Sci. USA* 32:120-128), an M63 medium (Miller, 1992; A Short Course in Bacterial Genetics: A Laboratory Manual and Handbook for *Escherichia coli* and Related Bacteria, Cold Spring Harbor Laboratory Press, Cold Spring Harbor, N.Y.) or a medium such as defined by Schaefer et al. (1999, *Anal. Biochem.* 270: 88-96).

As an example of known culture medium for *C. glutamicum*, the culture medium can be of identical or similar composition to BMCG medium (Liebl et al., 1989, *Appl. Microbiol. Biotechnol.* 32: 205-210) or to a medium such as described by Riedel et al. (2001, *J. Mol. Microbiol. Biotechnol.* 3: 573-583).

In a specific aspect of the invention, the culture is performed in such conditions that the microorganism is limited or starved for an inorganic substrate, in particular phosphate and/or potassium.

Subjecting an organism to a limitation of an inorganic substrate defines a condition under which growth of the microorganisms is governed by the quantity of an inorganic chemical supplied that still permits weak growth.

Starving a microorganism for an inorganic substrate defines the condition under which growth of the microorganism stops completely due, to the absence of the inorganic substrate.

The present invention is also related to a method for the production of methionine, comprising the step of isolation of methionine, its precursors or derivatives, of the fermentation broth and/or the biomass, optionally remaining in portions or in the total amount (0-100%) in the end product.

After fermentation L-methionine, its precursors or compounds derived thereof, is/are recovered and purified if necessary. The methods for the recovery and purification of the produced compound such as methionine and N-acetyl-methionine in the culture media are well known to those skilled in the art.

Optionally, from 0 to 100%, preferentially at least 90%, more preferentially 95%, even more preferentially at least 99% of the biomass may be retained during the purification of the fermentation product.

Optionally, the methionine derivative N-acetyl-methionine is transformed into methionine by deacylation, before methionine is recovered.

The present invention is also related to a modified microorganism comprising:
- a deletion of the MetJ gene,
- an expression of an allele MetA with reduced feeback sensitivity to methionine, and
- at least one of the modifications such as described above.

The present invention is also related to a modified microorganism such as described in the examples below.

DRAWING

FIG. 1 shows the metabolic pathway involving pyruvate, threonine, isoleucine and methionine.

Example I

Construction of strain MG1655 metA*11 Ptrc-metH
PtrcF-cysPUWAM PtrcF-cysJIH Ptrc09-gcvTHP
Ptrc36-ARNmst17-metF ΔmetJ ΔpykF ΔpykA
(pME101-thrA*1-cysE-PgapA-metA*11)

Methionine producing strains have been described in patent applications WO2007/077041 and WO2009/043372 which are incorporated as reference into this application.
1. Construction of the strain MG1655 metA*11 Ptrc-metH PtrcF-cysPUWAM PtrcF-cysJIH Ptrc09-gcvTHP Ptrc36-ARNmst17-metF ΔmetJ ΔpykF ΔpykA (pME101-thrA*1-cysE-PgapA-metA*11)
The plasmid pME101-thrA*1-cysE-PgapA-metA*11, described in the application WO2007/077041 and PCT/FR2009/052520, was introduced into the recombinant strain MG1655 metA*11 Ptrc-metH PtrcF-cysPUWAM PtrcF-cysJIH Ptrc09-gcvTHP Ptrc36-ARNmst17-metF ΔmetJ ΔpykF ΔpykA by electroporation, giving the strain MG1655 metA*11 Ptrc-metH PtrcF-cysPUWAM PtrcF-cysJIH Ptrc09-gcvTHP Ptrc36-ARNmst17-metF ΔmetJ ΔpykF ΔpykA (pME101-thrA*1-cysE-PgapA-metA*11).

Example II

Construction of strain MG1655 metA*11 Ptrc-metH
PtrcF-cysPUWAM PtrcF-cysJIH Ptrc09-gcvTHP
Ptrc36-ARNmst17-metF ΔmetJ ΔpykF ΔpykA ΔltaE
Δtdh (pME101-thrA*1-cysE-PgapA-metA*11)

Methionine producing strains have been described in patent applications WO2007077041 and WO2009/043372 which are incorporated as reference into this application.
1. Construction of the strain MG1655 metA*11 Ptrc-metH PtrcF-cysPUWAM PtrcF-cysJIH Ptrc09-gcvTHP Ptrc36-ARNmst17-metF ΔmetJ ΔpykF ΔpykA ΔltaE::Km
To inactivate the ltaE gene the homologous recombination strategy described by Datsenko & Wanner (2000) was used. This strategy allows the insertion of a kanamycin resistance cassette, while deleting most of the genes concerned. For this purpose 2 oligonucleotides, DltaEF and DltaER, were used (reference sequence on the Ecogen website.

DltaEF
(SEQ ID NO 1)
ggacatgccatgattgatttacgcagtgataccgttacccgaccaagcc gcgccatgctcgaagcgatgatggccgccccgTGTAGGCTGGAGCTGCT

TCG with
- a region (lower case) homologous to the sequence from 908446 to 908526 of the ltaE region,
- a region (upper case) for the amplification of the kanamycin resistance cassette (reference sequence in Datsenko, K. A. & Wanner, B. L., 2000, PNAS, 97: 6640-6645), DltaER
(SEQ ID NO 2)
gcgcaccagatgctgaccaatgtagccactggcaccgagaactaaaatg cgttgcggcacgtactctccttaacgcgccCATATGAATATCCTCCTTAG with
- a region (lower case) homologous to the sequence from 907446 to 907525 of the ltaE region, a region (upper case) for the amplification of the kanamycin resistance cassette.

The oligonucleotides DltaEF and DltaER were used to PCR amplify the kanamycin resistance cassette from the plasmid pKD4. The PCR product obtained was then introduced by electroporation into the strain MG1655 metA*11 Ptrc-metH PtrcF-cysPUWAM PtrcF-cysJIH Ptrc09-gcvTHP Ptrc36-ARNmst17-metF ΔmetJ ΔpykF ΔpykA (pKD46), in which the Red recombinase enzyme expressed permits the homologous recombination. The kanamycin resistant transformants were then selected and the insertion of the resistance cassette is verified by a PCR analysis with the oligonucleotides ltaEF and ltaER defined below. The strain retained was designated MG1655 metA*11 Ptrc-metH PtrcF-cysPUWAM PtrcF-cysJIH Ptrc09-gcvTHP Ptrc36-ARNmst17-metF ΔmetJ ΔpykF ΔpykA ΔltaE::Km.

ltaEF
(SEQ ID NO 3)
GCCACCTGGCGCTCCTGAGCG.
(homologous to the sequence from 907234 to 907254 of the ltaE region)

ltaER
(SEQ ID NO 4)
GCTGCGCGCAATCATCAGCGG.
(homologous to the sequence from 908603 to 908623 of the ltaE region)

2. Construction of the strain MG1655 metA*11 Ptrc-metH PtrcF-cysPUWAM PtrcF-cysJIH Ptrc09-gcvTHP Ptrc36-ARNmst17-metF ΔmetJ ΔpykF ΔpykA ΔltaE::Km Δtdh::Cm To inactivate the tdh gene the homologous recombination strategy described by Datsenko & Wanner (2000) was used. This strategy allows the insertion of a chloramphenicol resistance cassette, while deleting most of the genes concerned. For this purpose 2 oligonucleotides, Dtdhf and DtdhR, were used (reference sequence on the Ecogen website).

DtdhF
(SEQ ID NO 5)
gaaagcgttatccaaactgaaagcggaagagggcatctggatgaccga cgttcctgtaccggaactcgggcataacgatcCATATGAATATCCTCC

TTAG with
a region (lower case) homologous to the sequence from 3789287 to 3789366 of the tdh region,
a region (upper case) for the amplification of the chloramphenicol resistance cassette (reference sequence in Datsenko, K. A. & Wanner, B. L., 2000, PNAS, 97: 6640-6645), DtdhR
(SEQ ID NO 6)
cccagctcagaataactttcccggactggcccgaacgcatagcgtcaa agcccttctggaaatcatcgatagagaaacgatgggTGTAGGCTGGAG

CTGCTTCG with
a region (lower case) homologous to the sequence from 3788348 to 3788431 of the tdh region,
a region (upper case) for the amplification of the chloramphenicol resistance cassette.

The oligonucleotides DtdhF and DtdhR were used to PCR amplify the chloramphenicol resistance cassette from the plasmid pKD3. The PCR product obtained was then introduced by electroporation into the strain MG1655 metA*11 Ptrc-metH PtrcF-cysPUWAM PtrcF-cysJIH Ptrc09-gcvTHP Ptrc36-ARNmst17-metF ΔmetJ ΔpykF ΔpykA ΔltaE::Km (pKD46), in which the Red recombinase enzyme expressed permits the homologous recombination. The chloramphenicol resistant transformants were then selected and the insertion of the resistance cassette was verified by a PCR analysis with the oligonucleotides tdhF and tdhR defined below. The strain retained was designated MG1655 metA*11 Ptrc-metH PtrcF-cysPUWAM PtrcF-cysJIH Ptrc09-gcvTHP Ptrc36-ARNmst17-metF ΔmetJ ΔpykF ΔpykA ΔltaE::Km Δtdh::Cm.

tdhF
(SEQ ID NO 7)
GGGTAGAGAGATAATGAGAGCAGC.
(homologous to the sequence from 3788210 to 3788233 of the tdh region)

tdhR
(SEQ ID NO 8)
GCCCAGCCAAAACTGTACAG.
(homologous to the sequence from 3790719 to 3790738 of the tdh region)

3. Construction of the strain MG1655 metA*11 Ptrc-metH PtrcF-cysPUWAM PtrcF-cysJIH Ptrc09-gcvTHP Ptrc36-ARNmst17-metF ΔmetJ ΔpykF ΔpykA ΔltaE Δtdh The kanamycin and chloramphenicol resistance cassettes were then eliminated. The pCP20 plasmid, carrying recombinase FLP acting at the FRT sites of the kanamycin or chloramphenicol resistance cassette, was introduced into the recombinant strain MG1655 metA*11 Ptrc-metH PtrcF-cysPUWAM PtrcF-cysJIH Ptrc09-gcvTHP Ptrc36-ARNmst17-metF ΔmetJ ΔpykF ΔpykA ΔltaE::Km Δtdh::Cm by electroporation. After a series of cultures at 42° C., the loss of the kanamycin and chloramphenicol resistance cassettes was verified by PCR analysis with the same oligonucleotides as those used previously, ltaEF/ltaER and tdhF/tdhR. The strain retained was designated MG1655 metA*11 Ptrc-metH PtrcF-cysPUWAM PtrcF-cysJIH Ptrc09-gcvTHP Ptrc36-ARNmst17-metF ΔmetJ ΔpykF ΔpykA ΔltaE Δtdh.

4. Construction of the strain MG1655 metA*11 Ptrc-metH PtrcF-cysPUWAM PtrcF-cysJIH Ptrc09-gcvTHP Ptrc36-ARNmst17-metF ΔmetJ ΔpykF ΔpykA ΔltaE Δtdh (pME101-thrA*1-cysE-PgapA-metA*11)

The plasmid pME101-thrA*1-cysE-PgapA-metA*11, described in the application WO2007/077041 and PCT/FR2009/052520, was introduced into the recombinant strain MG1655 metA*11 Ptrc-metH PtrcF-cysPUWAM PtrcF-cysJIH Ptrc09-gcvTHP Ptrc36-ARNmst17-metF ΔmetJ ΔpykF ΔpykA ΔltaE Δtdh by electroporation, giving the strain MG1655 metA*11 Ptrc-metH PtrcF-cysPUWAM PtrcF-cysJIH Ptrc09-gcvTHP Ptrc36-ARNmst17-metF ΔmetJ ΔpykF ΔpykA ΔltaE Δtdh (pME101-thrA*1-cysE-PgapA-metA*11).

Example III

Evaluation of Production Strains

Production strains were evaluated in small Erlenmeyer flasks. A 5.5 mL preculture was grown at 37° C. for 16 hours in a mixed medium (10% LB medium (Sigma 25%) with 2.5 g·L$^{-1}$ glucose and 90% minimal medium PC1). It was used to inoculate a 50 mL culture to an OD$_{600}$ of 0.2 in medium PC1. Spectinomycin was added at a final concentration of 50 mg·L$^{-1}$. The temperature of the cultures was 37° C. When the culture had reached an OD$_{600}$ of 5 to 7, extracellular amino acids were quantified by HPLC after OPA/Fmoc derivatization and other relevant metabolites were analyzed using HPLC with refractometric detection (organic acids and glucose) and GC-MS after silylation. For each strain, three repetitions were made.

Strain 1 MG1655 metA*11 Ptrc-metH PtrcF-cysPUWAM PtrcF-cysJIH Ptrc09-gcvTHP Ptrc36-ARNmst17-metF ΔmetJ ΔpykF ΔpykA (pME101-thrA*1-cysE-PgapA-metA*11).

Strain 2 MG1655 metA*11 Ptrc-metH PtrcF-cysPUWAM PtrcF-cysJIH Ptrc09-gcvTHP Ptrc36-ARNmst17-metF ΔmetJ ΔpykF ΔpykA ΔltaE Δtdh (pME101-thrA*1-cysE-PgapA-metA*11).

TABLE 1

Minimal medium composition (PC1)

| Compound | Concentration (g · L$^{-1}$) |
| --- | --- |
| ZnSO$_4$•7H$_2$O | 0.0040 |
| CuCl$_2$•2H$_2$O | 0.0020 |
| MnSO$_4$•H$_2$O | 0.0200 |
| CoCl$_2$•6H$_2$O | 0.0080 |
| H$_3$BO$_3$ | 0.0010 |
| Na$_2$MoO$_4$•2H$_2$O | 0.0004 |
| MgSO$_4$•7H$_2$O | 1.00 |
| Citric acid | 6.00 |
| CaCl$_2$•2H$_2$O | 0.04 |
| K$_2$HPO$_4$•3H$_2$O | 10.50 |
| Na$_2$HPO$_4$ | 2.00 |
| (NH$_4$)$_2$HPO$_4$ | 8.00 |
| NH$_4$Cl | 0.13 |
| NaOH 4M | Adjusted to pH 6.8 |
| FeSO$_4$•7H$_2$O | 0.04 |
| Thiamine | 0.01 |
| Glucose | 10.00 |
| Ammonium thiosulfate | 5.60 |
| Vitamin B12 | 0.01 |
| MOPS | 10.00 |
| IPTG | 0.0024 |

TABLE 2

Methionine yield (Ymet) in % g methionine/g de glucose produced in batch culture by the different strains. For the exact definition of methionine/glucose yield see below.

| Strain | $Y_{met}$ | SD |
| --- | --- | --- |
| Strain 1: | 8.99 | 0.27 |
| Strain 2: | 9.56 | 0.3 |

SD denotes the standard deviation for the yield which was calculated on the basis of three repetitions.

Extracellular methionine concentration was quantified by HPLC after OPA/FMOC derivatization. The residual glucose concentration was analyzed using HPLC with refractometric detection. The methionine yield was expressed as follows:

$$Y_{met} = \frac{\text{methionine(g)}}{\text{consummed glucose(g)}} * 100$$

As can be seen in table 1 the methionine/glucose yield (Ymet) is increased upon the deletion of the genes tdh and ltaE.

Example IV

Construction of Methionine Production Strains 3 to 12 Tested in Examples V and VI Below 1. Protocols Several protocols have been used to construct methionine producing strains and are described in the following examples.

Protocol 1: Chromosomal modifications by homologous recombination and selection of recombinants (Datsenko, K. A. & Wanner, B. L. (2000)

Allelic replacement or gene disruption in specified chromosomal loci was carried out by homologous recombination as described by Datsenko. & Wanner (2000). The chloramphenicol (Cm) resistance cat, the kanamycin (Km) resistance kan, or the gentamycin (Gt) resistance gm genes, flanked by Flp recognition sites, were amplified by PCR by using pKD3 or pKD4 or p34S-Gm (Dennis et Zyltra, AEM July 1998, p 2710-2715) plasmids as template respectively. The resulting PCR products were used to transform the recipient E. coli strain harbouring plasmid pKD46 that expresses the λ Red (γ, β, exo) recombinase. Antibiotic-resistant transformants were selected and the chromosomal structure of the mutated loci was verified by PCR analysis with the appropriate primers listed in Table 4

The kan-resistance genes were removed by using plasmid pCP20 as described by Datsenko. & Wanner (2000), except that clones harboring the pCP20 plasmid were cultivated at 37° C. on LB and then tested for loss of antibiotic resistance at 30° C. Antibiotic sensitive clones were then verified by PCR using primers listed in Table 4

Protocol 2: P1 Phage Transduction

Chromosomal modifications were transferred to a given E. coli recipient strain by P1 transduction. The protocol is composed of 2 steps: (i) preparation of the phage lysate on a donor strain containing the chromosomal modification associated to the resistance gene and (ii) infection of the recipient strain by the resulting phage lysate.

Preparation of the Phage Lysate

Inoculate 100 μl of an overnight culture of the strain MG1655 with the chromosomal modification of interest in 10 ml of LB+Km 50 μg/ml or +glucose 0.2%+CaCl$_2$ 5 mM.

Incubate 30 min at 37° C. with shaking.

Add 100 μl of P1 phage lysate prepared on the donor strain MG1655 (approx. 1×10$^9$ phage/ml).

Shake at 37° C. for 3 hours until the complete lysis of cells.

Add 200 μl of chloroform, and vortex

Centrifuge 10 min at 4500 g to eliminate cell debris.

Transfer of supernatant to a sterile tube.

Store the lysate at 4° C.

Transduction

Centrifuge 10 min at 1500 g 5 ml of an overnight culture of the E. coli recipient strain cultivated in LB medium.

Suspend the cell pellet in 2.5 ml of MgSO$_4$ 10 mM, CaCl$_2$ 5 mM.

Infect 100 μl cells with 100 μl P1 phage lysate of the chromosomal modification strain MG1655 (test tube) and as a control tubes: 100 μl cells without P1 phage and 100 μl P1 phage without cells.

Incubate 30 min at 30° C. without shaking.
Add 100 μl sodium citrate 1 M to each tube, and vortex.
Add 1 ml of LB.
Incubate 1 hour at 37° C. with shaking
Centrifuge 3 min at 7000 rpm.
Plate on LB+Km 50 μg/ml
Incubate at 37° C. overnight.

The antibiotic-resistant transductants were then selected and the chromosomal structure of the mutated locus was verified by PCR analysis with the appropriate primers listed in Table 4.

Following examples describe the construction of all the strains listed in Table 3 below.

TABLE 3

List of genotypes and corresponding numbers of intermediate strains and producer strains that appear in the following examples.

| Strain number | Genotype |
|---|---|
| 3 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC sdaA*1 |
| 4 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC sdaA*1 ΔyobD::Km |
| 5 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC sdaA*1 ΔyobD::Km pCL1920-PgapA-pycRe-TT07 |
| 6 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC sdaArc ΔyobD::Km |
| 7 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC sdaArc ΔyobD::Km pCL1920-PgapA-pycRe-TT07 |
| 8 | MG1655 metA*11 Ptrc-metH PtrcF-cysPUWAM PtrcF-cysJIH Ptrc09-gcvTHP Ptrc36-ARNmst17-metF Ptrc07-serB ΔmetJ AΔykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC sdaA*1 ΔglyA::Km |
| 9 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC sdaA*1 ΔglyA::Km pCC1BAC-PglyA-glyA-TTglyA |
| 10 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC sdaA*1 ΔglyA::Km pCC1BAC-PglyA-glyA*(R235K)-TTglyA |
| 11 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC sdaA*1 ΔglyA::Km pCL1920-PglyA-glyA-TTglyA |
| 12 | MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-CI857-PlambdaR*(-35)-thrA*1-cysE ΔpgaABCD::TT02-TTadc-PlambdaR*(-35)-RBS01-thrA*1-cysE-PgapA-metA*11 |

TABLE 3-continued

List of genotypes and corresponding numbers of intermediate strains and producer strains that appear in the following examples.

| Strain number | Genotype |
|---|---|
| | ΔuxaCA ::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 DtreBC::TT02-serA-serC sdaA*1 ΔglyA ::Km pCL1920-PglyA-glyA* (R235K)-TTglyA |

2. Description of Strain 3

Genetic modifications of methionine producer strain 3 (Table 3) have been described in patent applications EP10306164.4 and U.S. 61/406,249 which are incorporated as reference into this application. After DNA sequencing of strain 3, a missense mutation has been identified unexpectedly in the sdaA gene. This mutation is located at position 158 of the structural gene (T158G) which generates an amino acid change in the corresponding protein: Leucine 53 to arginine. The allele was called sdaA*1.

3. Construction of Strains with a Modified sdaA Gene—Modification of the Serine Degradation Pathway 3.1. Construction of Strain 5 Containing sdaA*(T158G)

To delete the yobD gene in strain 3, Protocol 1 has been used except that primers Ome1983-DyobD-amplif-F (SEQ ID No09) and Ome 1986-DyobD-amplif-R (SEQ ID No10) (Table 4) were used to amplify the ΔyobD::Km deletion from strain BW25113 ΔyobD::Km (Keio collection Baba. et al., Mol Syst Biol., 2, 2006-0).

Kanamycin resistant recombinants were selected. The insertion of the resistance cassette was verified by PCR with primers Ome 1987-DyobD-verif-F (SEQ ID No11) and Ome 1988-DyobD-verif-R (SEQ ID No12) (Table 4) and by DNA sequencing. The sdaA*1 allele of sdaA gene was also verified by DNA sequencing. After elimination of plasmid pKD46, the resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 ΔtreBC::TT02-serA-serC sdaA*1 ΔyobD::Km was called strain 4 (Table 3).

The pCL1920-PgapA-pycRe-TT07, described in in patent applications EP10306164.4 and U.S. 61/406,249, was then introduced by electroporation into strain 4 (Table 3). The presence of plasmid pCL1920-PgapA-pycre-TTO7 was verified and the resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6:: TT02-TTadc-PlambdaR*(-35)-RBS01-thrA*1-cysE-PgapA-metA*11 ΔwcaM::TT02-TTadc-PlambdaR*(-35)-RBS01-thrA*1-cysE-PgapA-metA*11 ΔtreBC:: TT02-serA-serC sdaA*1 ΔyobD::Km pCL1920-PgapA-pycre-TT07 was called strain 5 (Table 3).

3.2. Construction of Strain 7 Containing a Reconstructed sdaAwt Allele (sdaArc)

The genes sdaA and yobD are close to each other on the E. coli chromosome; 40.84 min and 41.01 min respectively and since phage P1 can package 2 min of the E. coli chromosome, the genes sdaA and yobD are co-transducible. Thereby, the sdaA wild-type allele and ΔyobD::Km deletion, were co-transduced into strain 3 (Table 3) by using a P1 phage lysate from strain BW25113 sdaA ΔyobD::Km (Keio collection Baba. et al., Mol Syst Biol., 2, 2006-0) according to Protocol 2.

Kanamycin resistant transductants were selected. The presence of the ΔyobD::Km deletion was verified by PCR with primers Ome 1987-DyobD-verif-F (SEQ ID No11) and Ome 1988-DyobD-verif-R (SEQ ID No12) (Table 4) followed by DNA sequencing. The exchange of the sdaA*1 allele to the sdaA wild-type allele was verified by DNA sequencing and called sdaArc (rc for reconstructed). The resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR* (-35)-RBS01-thrA*1-cysE-PgapA-metA*11 ΔtreBC:: TT02-serA-serC sdaArc ΔyobD::Km was called strain 6 (Table 3).

The plasmid pCL1920-PgapA-pycre-TT07, described in in patent applications EP10306164.4 and U.S. 61/406,249, was then introduced by electroporation into strain 6 (Table 3). The presence of plasmid pCL1920-PgapA-pycre-TTO7 was verified and the resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(-35)-thrA*1-cysE ΔpgaABCD::TT02-TTadc-PlambdaR*(-35)-RBS01-thrA*1-cysE-PgapA-metA*11 ΔuxaCA::TT07-TTadc-PlambdaR*(-35)-RBS01-thrA*1-cysE-PgapA-metA*11 ΔCP4-6::TT02-TTadc-PlambdaR*(-35)-RBS01-thrA*1-cysE-PgapA-metA*11 ΔwcaM::TT02-TTadc-PlambdaR* (-35)-RBS01-thrA*1-cysE-PgapA-metA*11 ΔtreBC:: TT02-serA-serC sdaArc ΔyobD::Km pCL1920-PgapA-pycre-TTO7 was called strain 7 (Table 3).

4. Construction of Strains Overproducing Proteins GlyA or GlyA*(R235K)—Modification of the Threonine/Glycine Pathway 4.1. Construction of Strain 8 by Deletion of the glyA Gene To delete the glyA gene in strain 3, Protocol 1 has been used except that primers Ome 0641-DglyA R (SEQ ID No13) and Ome 0642-DglyA F (SEQ ID No14) (see below) were used to amplify the kanamycin resistance cassette from plasmid pKD4.

Kanamycin resistant recombinants were selected. The insertion of the resistance cassette was verified by PCR with primers Ome 0643-glyA R (SEQ ID No15) and Ome 0644-glyA F (SEQ ID No16) (Table 4) and by DNA sequencing. The resulting strain was called MG1655 metA*11 ΔglyA::Km pKD46.

Ome 0641-DglyA R (SEQ ID No 13)

ATGTTAAAGCGTGAAATGAACATTGCCGATTATGATGCCGAACTGTGGCA

GGCTATGGAGCAGGAAAAAGTACGTCAGG<u>TGTAGGCTGGAGCTGCTTCG</u> with
- upper case sequence homologous to sequence upstream of the glyA gene (2683451-2683529, reference sequence on the Ecogene website)
- underlined upper case sequence corresponding to the primer site 2 of plasmid pKD4 (Datsenko, K.A. & Wanner, B.L., 2000, PNAS, 97: 6640-6645)

Ome 0642-DglyA F (SEQ ID No 14)

GCGCAGATGTCGAGAACTTTACCTTTGATGCGCTCGATAACGGCTTCATC

ATTGATGCTGTCCAGCACGTCACACATCC<u>CATATGAATATCCTCCTTAG</u> with
- upper case sequence homologous to sequence upstream of the glyA gene (2682298-2682376, reference sequence on the Ecogene website)
- underlined upper case sequence corresponding to the primer site 1 of plasmid pKD4 (Datsenko, K.A. & Wanner, B.L., 2000, PNAS, 97: 6640-6645)

The ΔglyA::Km deletion was then transduced into strain 3 (Table 3) by using a P1 phage lysate from the strain MG1655 metA*11 ΔglyA::Km pKD46 described above according to Protocol 2.

Kanamycin resistant transductants were selected. The presence of the ΔglyA::Km deletion was verified by PCR with primers Ome 0643-glyA R (SEQ ID No15) and Ome 0644-glyA F (SEQ ID No16) (Table 4). The resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 DtreBC::TT02-serA-serC sdaA*1 ΔglyA::Km was called strain 8 (Table 3).

4.2. Construction of Strain 9 which Express glyA

In order to overexpress the serine hydroxymethyltransferase gene of *Escherichia coli*, plasmid pCC1BAC-PglyA-glyA-TTglyA was constructed, which is derived from plasmids pCC1BAC (EpiCentre) and pSCB (Stratagene).

To construct plasmid pCC1BAC-PglyA-glyA-TTglyA, the PglyA-glyA-TTglyA insert was amplified by PCR with primers Ome 1162-glyAR-EcoRI-HindIII (SEQ ID No17) and Ome 1165-PglyAF-HindIII (SEQ ID No18) using MG1655 genomic DNA as template and was cloned in plasmid pSCB (Stratagene). The resulting vector was verified by sequencing and called pSCB-PglyA-glyA-TTglyA.

Plasmid pSCB-PglyA-glyA-TTglyA was then digested by HindIII and the resulting fragment HindIII-PglyA-glyA-TTglyA-HindIII was cloned between the HindIII sites of plasmid pCC1BAC. The selected plasmid has the PglyA-glyA-TTglyA insert in the opposite orientation than the lacZ promoter of plasmid pCC1BAC, and was verified by DNA sequencing and called pCC1BAC-PglyA-glyA-TTglyA.

Ome 1162-glyAR-EcoRI-HindIII (SEQ ID No 17)

<u>ATCTAGTAAGCTTAGTGAATTCG</u>TTACGACAGATTTGATGGCGCG with
- underlined upper case sequence for HindIII and EcoRI restriction sites and extrabases,
- bold upper case sequence homologous to the glyA promoter sequence (2682063-682085, reference sequence on the Ecogene website).

Ome 1165-PglyAF-HindIII (SEQ ID No 18)

<u>TCATCGGATCCATCAAGCTT</u>GAAAGAATGTGATGAAGTG with
- underlined upper case sequence for BamHI and HindIII restriction sites and extrabases,
- bold upper case sequence homologous to the transcriptional terminator of the glyA gene (2683744-2683762), reference sequence on the Ecogene website).

The pCC1BAC-PglyA-glyA-TTglyA, described above, was then introduced by electroporation into strain 8 (Table 3). The presence of plasmid pCC1BAC-PglyA-glyA-TTglyA was verified and the resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 DtreBC::TT02-serA-serC sdaA*1 ΔglyA::Km pCC1BAC-PglyA-glyA-TTglyA was called strain 9 (Table 3).

4.3. Construction of Strain 10 which Expresses glyA*

Construction of pSCB-PglyA-glyA*(R235K)-TTglyA

To construct plasmid pCC1BAC-PglyA-glyA*(R235K)-TTglyA, plasmid pSCB-PglyA-glyA-TTglyA was amplified with primers Ome 1483-glyA*R R235K (SEQ ID No19) and Ome 1482-glyA*F R235K (SEQ ID No20). The PCR product was digested by DpnI in order to eliminate the parental DNA template. The remaining cohesive overhang was phosphorylated and introduced in an *E. coli* strain to form plasmid pSCB-PglyA-glyA*(R235K)-TTglyA. The PglyA-glyA*(R235K)-TTglyA insert and especially the presence of the R235K (703-AAA-705) mutation in the glyA gene were verified by DNA sequencing.

Ome 1483 glyA* R R235K (SEQ ID No 19)

CCTTTCGCCAGGATCAGGCC<u>T</u>CCTTTCGGACCCGCCAGGGTTTTGTGAG

With
- upper case sequence homologous to the glyA gene (2682802-2682850, reference sequence on the Ecogene website).
- bold upper cases corresponding to the inserted codon mutation CGC-708-TTT (R235K)

underlined upper case corresponding to a silent point mutation (G704T) which makes appear a StuI restriction site.

Ome 1482 glyA* F R235K
(SEQ ID No 20)
CTCACAAAACCCTGGCGGGTCCGAAAGG<u>A</u>GGCCTGATCCTGGCGAAAGG upper case sequence homologous to the glyA gene (2682802-2682850, reference sequence on the Ecogene website).

bold upper cases corresponding to the inserted codon mutation CGC-708-TTT (R235K)

underlined upper case corresponding to a silent point mutation (G704T) which makes appear a StuI restriction site.

Construction of pCC1BAC-PglyA-glyA*(R235K)-TTglyA

To construct pCC1BAC-PglyA-glyA*(R235K)-TTglyA, the HindIII fragment PglyA-glyA*(R235K)-TTglyA purified from pSCB-PglyA-glyA*(R235K)-TTglyA, described below, was cloned between the HindIII sites of plasmid pCC1BAC. The selected plasmid has the PglyA-glyA*(R235K)-TTglyA insert in the opposite orientation compared to the lacZ promoter orientation of plasmid pCC1BAC, was verified by DNA sequencing and called pCC1BAC-PglyA-glyA*(R235K)-TTglyA.

The pCC1BAC-PglyA-glyA*(R235K)-TTglyA, described above, was then introduced by electroporation into strain 8 (Table 3). The presence of plasmid pCC1BAC-PglyA-glyA*(R235K)-TTglyA was verified and the resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 DtreBC::TT02-serA-serC sdaA*1 ΔglyA::Km pCC1BAC-PglyA-glyA*(R235K)-TTglyA was called strain 10 (Table 3).

4.4. Construction of Strain 11 which Overexpresses glyA
Construction of pCL1920-PglyA-glyA-TTglyA Plasmid pCL1920-PglyA-glyA-TTglyA is derived from plasmid pCL1920 (Lerner & Inouye, 1990, NAR 18, 15 p 4631) and pCC1BAC-PglyA-glyA-TTglyA described above.

To construct pCL1920-PglyA-glyA-TTglyA, the HindIII fragment PglyA-glyA-TTglyA purified from pCC1BAC-PglyA-glyA-TTglyA was cloned between the HindIII sites of plasmid pCL1920. The selected plasmid has the PglyA-glyA-TTglyA insert in the opposite orientation compared to the lacZ promoter orientation of plasmid pCL1920, was verified by DNA sequencing and called pCL1920-PglyA-glyA-TTglyA.

The pCL1920-PglyA-glyA-TTglyA, described above, was then introduced by electroporation into strain 8 (Table 3). The presence of plasmid pCL1920-PglyA-glyA-TTglyA was verified and the resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(−35)-thrA*1-cysE ΔpgaABCD::TT02-TTadc-PlambdaR*(−35)-RBS01-thrA*1-cysE-PgapA-metA*11 ΔuxaCA::TT07-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 DtreBC::TT02-serA-serC sdaA*1 ΔglyA::Km pCL1920-PglyA-glyA-TTglyA was called strain 11 (Table 3).

4.5. Construction of Strain 12 which Overexpresses glyA*
Construction of pCL1920-PglyA-glyA*(R235K)-TTglyA Plasmid pCL1920-PglyA-glyA*(R235K)-TTglyA is derived from plasmid pCL1920 (Lerner & Inouye, 1990, NAR 18, 15 p 4631) and pCC1BAC-PglyA-glyA*(R235K)-TTglyA described above.

To construct pCL1920-PglyA-glyA*(R235K)-TTglyA, the HindIII fragment PglyA-glyA*(R235K)-TTglyA purified from pCC1BAC-PglyA-glyA*(R235K)-TTglyA, was cloned between the HindIII sites of plasmid pCL1920. The selected plasmid which has the PglyA-glyA*(R235K)-TTglyA insert in the opposite orientation compared to the lacZ promoter orientation of pCL1920 plasmid, was verified by DNA sequencing and called pCL1920-PglyA-glyA*(R235K)-TTglyA.

The pCL1920-PglyA-glyA*(R235K)-TTglyA, was then introduced by electroporation into strain 8 (Table 3). The presence of plasmid pCC1BAC-PglyA-glyA*(R235K)-TTglyA was verified and the resulting strain MG1655 metA*11 Ptrc-metH PtrcF-cysPUWAM PtrcF-cysJIH Ptrc09-gcvTHP Ptrc36-ARNmst17-metF Ptrc07-serB ΔmetJ ΔpykF ΔpykA ΔpurU ΔyncA ΔmalS::TTadc-C1857-PlambdaR*(−35)-thrA*1-cysE ΔpgaABCD::TT02-TTadc-PlambdaR*(−35)-RBS01-thrA*1-cys E-PgapA-metA*11 ΔuxaCA::TTO7-TTadc-PlambdaR*(−35)-RBS01-thrA*1-cysE-PgapA-metA*11 ΔCP4-6::TT02-TTadc-PlambdaR*(−35)-RBS01-thrA*1-cysE-PgapA-metA*11 ΔwcaM::TT02-TTadc-PlambdaR*(−35)-RBS01-thrA*1-cysE-PgapA-metA*11 DtreBC::TT02-serA-serC sdaA*1 ΔglyA::Km pCL1920-PglyA-glyA*(R235K)-TTglyA was called strain 12 (Table 3).

TABLE 4

Primers used for PCR verifications of chromosomal modifications described above

| Genes name | Primers name | SED ID N° | Location of the homology with the chromosal region | Sequences |
|---|---|---|---|---|
| yobD | Ome 1983-DyobD-amplif-F | 9 | 1902261-1902280 | CTGGCTGGTGTAGGCGACCC |
|  | Ome 1986-DyobD-amplif-R | 10 | 1903864-1903883 | CCATTCCCCAGCCGATCAGC |
|  | Ome 1987-DyobD-verif-F | 11 | 1902185-1902207 | GGAAGAACAGCGTGCTAATGGCG |
|  | Ome 1988- DyobD-verif-R | 12 | 1903984-1904008 | CGGCTCTTCATCTTCATCATCTGCG |

TABLE 4-continued

Primers used for PCR verifications of chromosomal modifications described above

| Genes name | Primers name | SED ID N° | Location of the homology with the chromosal region | Sequences |
|---|---|---|---|---|
| glyA | Ome 0643-glyA R | 15 | 2683575-2683597 | CGCCGTTGTCCAACAGGACCGCC |
|  | Ome 0644-glyA F | 16 | 2682140-2682159 | CCTGATGCGCTACGCTTATC |

Example V

Effect of the Attenuation of Threonine Aldolase Activity of a GLYA* Mutant Protein on the Methionine Production 1. Evaluation of Production Strains Having Either glyA or glyA* Allele Production strains were evaluated in small Erlenmeyer flasks. A 5.5 mL preculture was grown at 30° C. for 21 hours in a mixed medium (10% LB medium (Sigma 25%) with 2.5 g·L$^{-1}$ glucose and 90% minimal medium PC1). It was used to inoculate a 50 mL culture to an OD600 of 0.2 in medium PC1 (composition in Table 5). Kanamycin and spectinomycin were added at a concentration of 50 mg·L$^{-1}$ and chloramphenicol at 30 mg·L$^{-1}$ when it was necessary. The temperature of the cultures was 37° C. When the culture had reached an OD600 of 5 to 7, extracellular amino acids were quantified by HPLC after OPA/Fmoc derivatization and other relevant metabolites were analyzed using HPLC with refractometric detection (organic acids and glucose) and GC-MS after silylation.

TABLE 5

Minimal medium composition (PC1).

| Compound | Concentration (g · L$^{-1}$) |
|---|---|
| ZnSO$_4$•7H$_2$O | 0.0040 |
| CuCl$_2$•2H$_2$O | 0.0020 |
| MnSO$_4$•H$_2$O | 0.0200 |
| CoCl$_2$•6H$_2$O | 0.0080 |
| H$_3$BO$_3$ | 0.0010 |
| Na$_2$MoO$_4$•2H$_2$O | 0.0004 |
| MgSO$_4$•7H$_2$O | 1.00 |
| Citric acid | 6.00 |
| CaCl$_2$•2H$_2$O | 0.04 |
| K$_2$HPO$_4$ | 8.00 |
| Na$_2$HPO$_4$ | 2.00 |
| (NH$_4$)$_2$HPO$_4$ | 8.00 |
| NH$_4$Cl | 0.13 |
| NaOH 4M | Adjusted to pH 6.8 |
| FeSO$_4$•7H$_2$O | 0.04 |
| Thiamine | 0.01 |
| Glucose | 15.00 |
| Ammonium thiosulfate | 5.61 |
| Vitamin B12 | 0.01 |

TABLE 6

Methionine yield ($Y_{met}$) in % g methionine/g glucose produced in batch culture by different strains grown in conditions described above. For the precise definition of methionine/glucose yield see below.

| strain | $Y_{met}$ | SD | N |
|---|---|---|---|
| Strain 3 | 9.75 | 1.29 | 110 |
| Strain 9 - glyA wt allele | 9.80 | 0.19 | 3 |
| Strain 10 - glyA* allele | 10.53 | 0.53 | 3 |
| Strain 11 - glyA wt allele | 10.95 | 0.35 | 3 |
| Strain 12 - glyA* allele | 11.89 | 0.66 | 3 |

SD denotes the standard deviation for the yields that was calculated on the basis of several repetitions (N = number of repetitions).

In addition to catalyzing the transformation of serine into glycine, the GlyA enzyme is also able to cleave L-threonine. That was demonstrated by the inventors with a strain carrying a glyA deletion. This strain had no detectable Serine HydroxyMethylTransferase (SHMT) and Threonine ALdolase (TAL) activities anymore (data not shown).

As can be seen in table 6 the methionine/glucose yield (Ymet) is increased upon expression (strain 10) or overexpression (strain 12) of the glyA* allele compared to glyAwt (respectively strain 9 and 11 for expression and overexpression of glyAwt).

The attenuation of threonine aldolase activity without affecting the serine hydroxymethyltransferase (SHMT) of GlyA is beneficial for the production of methionine (see activities in table 7 below).

Extracellular methionine concentration was quantified by HPLC after OPA/FMOC derivatization. The residual glucose concentration was analyzed using HPLC with refractometric detection. The methionine yield was expressed as follows:

$$Y_{met} = \frac{\text{methionine(g)}}{\text{consumed glucose(g)}} * 100$$

2. Determination of SHMT and TAL Activities of Strains Overexpressing Either glyA wt or glyA* Allele For the in vitro determination of Serine HydroxyMethylTransferase (SHMT), Threonine ALdolase (TAL) and allo-Threonine ALdolase (aTAL) activities, E. coli strains were cultured in minimal medium as described above and biomass was harvested at end log phase by centrifugation. Pellets were resuspended in cold 20 mM potassium phosphate buffer pH 7.2 containing a cocktail of protease inhibitors with EDTA. Then, cells were lysed by bead beating with a Precellys (Bertin Technologies; 2×10 s at 6500 rpm) followed by centrifugation at 12000 g at 4° C. for 30 minutes. Supernatants were desalted and used for enzymatic analyses. Protein concentrations were determined using Bradford assay reagent (Bradford, 1976).

SHMT activity was monitored spectrophotometrically at 37° C. using a Methylene TetraHydroFolate Dehydrogenase (MTHFD) coupled enzyme assay as described in equations (1) and (2). In this assay, the formation of 5,10-methenyl-THF yielded by the oxidation of 5,10-methylene-THF produced by the SHMT enzyme reaction was monitored at 350 nm.

$$\text{L-Serine} + \text{THF} + 2\text{H}^+ \leftrightarrow \text{Glycine} + 5,10\text{-methylene-THF (SHMT reaction)} \quad (1)$$

$$5,10\text{-methylene-THF} + \text{NADP}^+ \leftrightarrow 5,10\text{-methenyl-THF} + \text{NADPH (MTHFD reaction)} \quad (2)$$

For the determination of SHMT activity, 2 µg of crude cell extracts were assayed in 50 mM Bicine-KOH buffer pH 8.6, 10 mM L-serine, 0.4 mM THF, 10 mM 2-mercaptoethanol, and 1.5 mM NADP$^+$. After incubation for 10 minutes at 37° C., the reaction was started by the addition of crude cell extract and the purified MTHFD enzyme from E. coli. Then, the reaction mixture was incubated for 10 minutes at 37° C. and the reaction was stopped by the addition of 2% (v/v) perchloric acid. Addition of perchloric acid destroys the reduced pyridine nucleotide formed in the reaction (2). After 10 minutes at room temperature, the absorbance was read at 350 nm. In every experiment, a control without L-serine was run and used as a blank for the spectrophotometric measurements.

TAL activity generating glycine plus acetaldehyde was assayed fluorimetrically at 37° C. using the 4-hydrazino-7-nitrobenzofurazane (NBDH) detection system. The rate of formation of acetaldehyde was determined by derivatization of acetaldehyde produced with NBDH to yield a fluorescent hydrazone derivative at 530 nm. 200-250 µg of crude cell extracts were assayed in 20 mM HEPES-HCl buffer pH8.0, 0.01 mM pyridoxal phosphate, and 10 mM L-threonine. The reaction was started by the addition of the crude cell extract. After incubation at 37° C. for 10 and 40 minutes, the reaction was stopped by the addition of 2.5% (v/v) TCA. After centrifugation 5 minutes at 10000 g at room temperature, 0.001% (w/v) NBDH in 0.33M sodium acetate pH5.2 was added to the supernatant and the fluorescent hydrazones produced were quantified after 10 minutes incubation at room temperature with a FLx800 Fluorescence Microplate Reader (λexcitation=485 nm; λemission=530 nm, Biotek). In every experiment, a control without L-threonine was run and use as a blank for the fluorimetric measurements.

TABLE 7

Serine hydroxymethyltransferase (SHMT) and threonine aldolase (TAL) activities were determined for different strains and are given in mUI/mg of protein.

| Strain | SHMT | TAL | N |
|---|---|---|---|
| Strain 3 | 921 ± 1 | 9.2 ± 0.4 | 3 |
| Strain 9 - glyA wt allele | 1078 ± 55 | 9.8 ± 0.8 | 3 |
| Strain 10 - glyA* allele | 875 ± 30 | 4.6 ± 0.5 | 3 |
| Strain 11 - glyA wt allele | 3908 ± 42 | 50.5 ± 2.2 | 3 |
| Strain 12 - glyA* allele | 3721 ± 46 | 8.7 ± 0.6 | 3 |

Standard deviations were calculated on the basis of several independent cultures (N = number of replicates).

As can be seen in table 7, the TAL activity of strains 10 and 12 (with glyA*) were respectively about 2 and 6 fold smaller than those of the control strains 3, 9 and strain 11 (with glyAwt). Moreover, the R235K mutation introduced in the GlyA enzyme leading to GlyA* decreased TAL activity without affecting drastically its SHMT activity with respect to the wild-type enzyme. The attenuation of threonine aldolase activity without affecting the main Serine hydroxymethyltransferase (SHMT) activity of GlyA is beneficial for the production of methionine (see methionine yield in previous table 6).

This may enhance the carbon flux from serine to glycine in strain 10 and 12 compared to strains 3, and 11 and is in good agreement with methionine production results (table 6).

Example VI

Effect of the Attenuation of Serine Deaminase Activity (SDA) on the Methionine Production 1. Evaluation of Production Strains Having Either sdaArc (Strain 7) or sdaA* (Strain 5)

Strains were tested under production conditions in 2.5 L fermentors (Pierre Guerin) using a fedbatch strategy.

Kanamycin and spectinopycin were added at a concentration of 50 mg·L-1 in each media. Briefly, an 24 hour culture grown in 10 mL LB medium with 2.5 g·L-1 glucose was used to inoculate a 24 hour preculture in minimal medium (B1 a). These incubations were carried out in 500 mL baffled flasks containing 50 mL of minimal medium (B1 a) in a rotary shaker (200 RPM). The first preculture was grown at a temperature of 30° C., the second one at a temperature of 34° C.

A third preculture step was carried out in bio-reactors (Sixfors) filled with 200 mL of minimal medium (B1b) inoculated to a biomass concentration of 1.2 g·L$^{-1}$ with 5 mL concentrated preculture. The preculture temperature was maintained constant at 34° C. and the pH was automatically adjusted to a value of 6.8 using a 10% NH$_4$OH solution. The dissolved oxygen concentration was continuously adjusted to a value of 30% of the partial air pressure saturation with air supply and/or agitation. After glucose exhaustion from the batch medium, the fedbatch was started with an initial flow rate of 0.7 mL·h$^{-1}$, increased exponentially for 24 hours with a growth rate of 0.13 h$^{-1}$ in order to obtain a final cellular concentration of about 18 g·L$^{-1}$.

TABLE 8

Preculture batch mineral medium composition (B1a and B1b).

| Compound | B1a Concentration (g · L$^{-1}$) | B1b Concentration (g · L$^{-1}$) |
|---|---|---|
| Zn(CH$_3$COO)$_2$.2H$_2$O | 0.0130 | 0.0130 |
| CuCl$_2$.2H$_2$O | 0.0015 | 0.0015 |
| MnCl$_2$.4H$_2$O | 0.0150 | 0.0150 |
| CoCl$_2$•6H$_2$O | 0.0025 | 0.0025 |
| H$_3$BO$_3$ | 0.0030 | 0.0030 |
| Na$_2$MoO$_4$•2H$_2$O | 0.0025 | 0.0025 |
| Fe(III) citrate H$_2$O | 0.1064 | 0.1064 |
| EDTA | 0.0084 | 0.0084 |
| MgSO$_4$•7H$_2$O | 1.00 | 1.00 |
| CaCl$_2$.2H$_2$O | 0.08 | 0.08 |
| Citric acid | 1.70 | 1.70 |
| KH$_2$PO$_4$ | 4.57 | 4.57 |
| K$_2$HPO$_4$.3H$_2$O | 2.54 | 2.54 |
| (NH$_4$)$_2$HPO$_4$ | 1.11 | 1.11 |
| (NH$_4$)$_2$SO$_4$ | 4.90 | 4.90 |
| (NH$_4$)$_2$S$_2$O$_3$ | 1.00 | 1.00 |
| Thiamine | 0.01 | 0.01 |
| Vitamin B12 | 0.01 | 0.01 |
| Glucose | 30.00 | 5.00 |
| MOPS | 30.00 | 0.00 |
| NH$_4$OH 28% | Adjusted to pH 6.8 | Adjusted to pH 6.8 |

TABLE 9

Preculture fedbatch mineral medium composition (F1)

| Compound | Concentration (g · L$^{-1}$) |
|---|---|
| Zn(CH$_3$COO)$_2$•H$_2$O | 0.0104 |
| CuCl$_2$•2H$_2$O | 0.0012 |
| MnCl$_2$•4H$_2$O | 0.0120 |
| CoCl$_2$•6H$_2$O | 0.0020 |
| H$_3$BO$_3$ | 0.0024 |
| Na$_2$MoO$_4$•2H$_2$O | 0.0020 |
| Fe(III) citrate H$_2$O | 0.0424 |
| EDTA | 0.0067 |
| MgSO$_4$ | 5.00 |
| (NH$_4$)$_2$SO$_4$ | 8.30 |
| Na$_2$SO$_4$ | 8.90 |
| (NH$_4$)$_2$S$_2$O$_3$ | 24.80 |
| Thiamine | 0.01 |
| Glucose | 500.00 |
| Vitamin B12 | 0.01 |
| NH$_4$OH 28% | Adjusted to pH 6.8 |

TABLE 10

Culture batch mineral medium composition (B2).

| Compound | Concentration (g · L$^{-1}$) |
|---|---|
| Zn(CH$_3$COO)$_2$•2H$_2$O | 0.0130 |
| CuCl$_2$•2H$_2$O | 0.0015 |
| MnCl$_2$•4H$_2$O | 0.0150 |
| CoCl$_2$•6H$_2$O | 0.0025 |
| H$_3$BO$_3$ | 0.0030 |
| Na$_2$MoO$_4$•2H$_2$O | 0.0025 |
| Fe(III) citrate H$_2$O | 0.1064 |
| EDTA | 0.0084 |
| MgS$_2$O$_3$•6H$_2$O | 1.00 |
| CaCl$_2$•2H$_2$O | 0.08 |
| Citric acid | 1.70 |
| KH$_2$PO$_4$ | 2.97 |
| K$_2$HPO$_4$•3H$_2$O | 1.65 |
| (NH$_4$)$_2$HPO$_4$ | 0.72 |
| (NH$_4$)$_2$S$_2$O$_3$ | 3.74 |
| Thiamine | 0.01 |
| Vitamin B12 | 0.01 |
| Biotin | 0.10 |
| Glucose | 10 |
| NH$_4$OH 28% | Adjusted to pH 6.8 |

TABLE 11

Culture fedbatch medium composition (F2).

| Compound | Concentration (g · L$^{-1}$) |
|---|---|
| Zn(CH$_3$COO)$_2$•2H$_2$O | 0.0104 |
| CuCl$_2$•2H$_2$O | 0.0012 |
| MnCl$_2$•4H$_2$O | 0.0120 |
| CoCl$_2$•6H$_2$O | 0.0020 |
| H$_3$BO$_3$ | 0.0024 |
| Na$_2$MoO$_4$•2H$_2$O | 0.0020 |
| Fe(III) citrate H$_2$O | 0.0524 |
| EDTA | 0.0067 |
| MgS$_2$O$_3$•6H$_2$O | 10.20 |
| (NH$_4$)$_2$S$_2$O$_3$ | 55.50 |
| Thiamine | 0.01 |
| Vitamin B12 | 0.01 |
| Biotin | 0.10 |
| Glucose | 500 |

Subsequently, 2.5 L fermentors (Pierre Guerin) were filled with 600 mL of minimal medium (B2) and were inoculated to a biomass concentration of 2.1 g·L$^{-1}$ with a preculture volume ranging between 55 to 70 mL.

The culture temperature was maintained constant at 37° C. and pH was maintained at the working value (6.8) by automatic addition of NH$_4$OH solutions (NH$_4$OH 10% for 9 hours and 28% until the culture end). The initial agitation rate was set at 200 RPM during the batch phase and was increased up to 1000 RPM during the fedbatch phase. The initial airflow rate was set at 40 NL·h$^{-1}$ during the batch phase and was increase to 100 NL·h$^{-1}$ at the beginning of the fedbatch phase. The dissolved oxygen concentration was maintained at values between 20 and 40%, preferentially 30% saturation by increasing the agitation.

When the cell mass reached a concentration close to 5 g·L$^{-1}$, the fedbatch was started with an initial flow rate of 5 mL·h$^{-1}$. Feeding solution was injected with a sigmoid profile with an increasing flow rate that reached 24 mL·h$^{-1}$ after 26 hours. The precise feeding conditions were calculated by the equation:

$$Q(t) = p1 + \frac{p2}{1 + e^{-p3(t-p4)}}$$

where Q(t) is the feeding flow rate in mL·h$^{-1}$ for a batch volume of 600 mL with p1=1.80, p2=22.40, p3=0.270, p4=6.5.

After 26 hours fedbatch, the feeding solution pump was stopped and the culture was stopped after glucose exhaustion.

Extracellular amino acids were quantified by HPLC after OPA/Fmoc derivatization and other relevant metabolites were analyzed using HPLC with refractometric detection (organic acids and glucose) and GC-MS after silylation.

TABLE 12

Maximal methionine yield ($Y_{met\ max}$) in % g of methionine per g of glucose produced in fedbatch culture by strains. For the definition of methionine/glucose yield see below.

| Strain | $Y_{met\ max}$ | SD | N |
|---|---|---|---|
| Strain 7 - sdaArc allele | 22.4 | 0.2 | 2 |
| Strain 5 - sdaA* allele | 23.9 | nd | 1 |

SD denotes the standard deviation for the yields which was calculated on the basis of several repetitions (N = number of repetitions).

As can be seen in table 12 the methionine/glucose yield (Ymet) is increased upon expression of sdaA* allele compared to expression of sdaAwt. The attenuation of the serine deaminase activity of SdaA enzyme increase serine availability for methionine production.

The fermentor volume was calculated by adding to the initial volume the amount of solutions added to regulate the pH and to feed the culture and by subtracting the volume used for sampling and lost by evaporation.

The fedbatch volume was followed continuously by weighing the feeding stock. The amount of injected glucose was then calculated on the basis of the injected weight, the density of the solution and the glucose concentration determined by the method of Brix ([Glucose]).

The methionine yield was expressed as followed:

$$Y_{met} = \frac{\text{Methionine}_t * V_t - \text{Methionine}_0 * V_0 \times 100}{\text{Consumed glucose}_t}$$

The maximal yield obtained during the culture was presented here for each strain.

With Methionine$_0$ and Methionine$_t$ respectively the initial and final methionine concentrations and V$_0$ and V$_t$ the initial and the instant t volumes.

The consumed glucose was calculated as follows:

$$\text{fed volume}_t = \frac{\text{fed weight}_0 - \text{fed weight}_t}{\text{density fed solution}}$$

Injected Glucose$_t$=fed volume$_t$*[Glucose]

Consumed glucose$_t$=[Glucose]$_0$*V$_0$+Injected Glucose–[Glucose]$_{residual}$*V$_t$ With [Glucose]$_0$, [Glucose], [Glucose]$_{residual}$ respectively the initial, the fed and the residual glucose concentrations.

2. Determination of Serine DeAminase Activity (SDA) in Strains 5 and 7

For the in vitro determination of SDA activity, E. coli strains were cultured in minimal medium as described above and harvested by centrifugation. Pellets were suspended in cold 50 mM glycylglycine buffer (pH 8) with 3 mM FeSO$_4$, 30 mM DTT and a cocktail of EDTA-free protease inhibitors. Then, cells were lysed by bead beating with a Precellys (Bertin Technologies; 2×10 s at 6500 rpm) followed by centrifugation at 12000 g (4° C.) for 30 minutes. Supernatants were not desalted and used for enzymatic analysis. Protein concentrations were determined using Bradford assay reagent (Bradford, 1976).

For the determination of SDA activity, 100 µg of crude cell extracts were assayed in 50 mM glycylglycine buffer (pH 8) with 3 mM FeSO$_4$, 30 mM DTT and 50 mM L-serine. The reaction was started by adding the crude cell extracts. After incubation at 37° C. for 5 and 20 minutes, 0.4 mL of toluene were added and the reaction was stopped with 2-4-dinitrophenylhydrazine in HCl. After homogenization, the preparation mixture was centrifuged 5 minutes at 3500 rpm at room temperature and the upper phase was treated with 10% (w/v) sodium carbonate. After homogenization, the preparation mixture was centrifuged 1 minute at 3500 rpm at room temperature and the lower phase was treated with 1.5M NaOH. After 10 minutes incubation, the amount of pyruvate produced was determined spectrophotometrically at 540 nm by the measurement of the colour of the keto-acid hydrazone in the alkaline solution. The colour intensity did not change within a 15 minutes period. In every experiment, a control without L-serine was run and use as a blank for the spectrophotometric measurements.

TABLE 13

Serine deaminase (SDA) activities were determined in the above described cultures and were given in mUI/mg of proteins.

| Strain | SDA | N |
| --- | --- | --- |
| Strain 7 - sdaArc allele | 1517 ± 142 | 2 |
| Strain 5 - sdaA* allele | 12.4 | 1 |

Standard deviations were calculated on the basis of several independent cultures (N = number of replicates).

As can be seen in table 13 the SDA activity of the strain 5 is more than 100 times lower than that of the wild-type strain 7. This significant decrease of SDA activity was correlated to an improvement of methionine production (see table 12).

It is important to notice that there is a residual serine deaminase activity with SdaA*, this may be important for the physiology of the cell.

REFERENCES

1. Anderson, 1946, Proc. Natl. Acad. Sci. USA 32, 120-128
2. Angelaccio S, Pascarella S, Fattori E, Bossa F, Strong W, Schirch V, 1992, Biochemistry, 31, 155-162
3. Boylan S A, Dekker E E, 1981, Journal of Biological Chemistry, 256(4), 1809-1815
4. Carrier and Keasling, 1998, Biotechnol. Prog., 15, 58-64
5. Datsenko, K A & Wanner B L, 2000, PNAS, 97: 6640-6645
6. Goss T J, Schweizer H P, Datta P, 1988, J Bacteriol, 170, 5352-5359
7. Komatsubara S, Murata K, Kisumi M, Chibata I, 1978, Journal of Bacteriology, 1981, 135, 318-323
8. Lee et al, 2007, Molecular Systems Biology, 3(149), pp 1-8
9. Liebl W, Klamer R, Schleifer K H, 1989, Appl. Microbiol. Biotechnol, 32, 205-210
10. Liu J Q, Dairi T, Itoh N, Kataoka M, Shimizu S, Yamada H, 1998, European Journal of Biochemistry, 255(1), 220-226
11. Liu J Q, Dairi T, Itoh N, Kataoka M, Shimizu S, Yamada H, 1998, European Journal of Biochemistry, 255(1), 220-226
12. Marcus J P, Dekker E E, 1993, Biochemica et Biophysica Acta, 1164, 299-304
13. Markus J P, Dekker E E, 1993, Biochemica et Biophysica Acta, 1164, 299-304
14. Martinez-Force et al, 1994, Biotechnolgy Progress, 10(4), pp 372-376
15. Miller, 1992; A Short Course in Bacterial Genetics: A Laboratory Manual and Handbook for Escherichia coli and Related Bacteria, Cold Spring Harbor Laboratory Press, Cold Spring Harbor, N.Y.
16. Mukherjee J J, Dekker E E, 1987, Journal of Biological Chemistry, 262(30), 14441-14447
17. Mukherjee J J, Dekker E E, 1987, Journal of Biological Chemistry, 262(30), 14441-14447
18. Plamann M D, Stauffer G V, 1983, Gene, 22(1), 9-18
19. Ramakrishnan T, Adelberg E A, 1965, J Bacteriol, 89, 661-664
20. Riedel C, Rittmann D, Dangel P, Möckel B, Petersen S, Sahm H, Eikmanns B J, 2001, J. Mol. Microbiol. Biotechnol. 3, 573-583
21. Saunderson C L, (1985) British Journal of Nutrition 54, 621-633
22. Scarsdale J N, Radaev S, Kazanina G, Schirch V, Wright H T, 2000, Journal of Molecular Biology, 296, 155-168
23. Schaefer U, Boos W, Takors R, Weuster-Botz D, 1999, Anal. Biochem, 270, 88-96
24. Schirch L, 1982, Advances in enzymology and related areas of molecular biology, 53, 83-112
25. Schirch V, Gross T, 1968, Journal of Biological Chemistry, 243, 5651-5655
26. Schirch V, Hopkins S, Villar E, Angelaccio S, 1985, Journal of Bacteriology, 163(1), 1-7
27. Schirch V, Szebenyi D M, 2005, Current opinion in Chemical biology, 9, 482-487
28. Simic et al, 2002, Applied and Environmental microbiology, 68(7), pp 3321-3327
29. Su H S and Newman E B, 1991, J Bacteriol, 173, 2473-2480
30. Su H S, Lang B F, Newman E B, 1989, J Bacteriol, 171, 5095-5102.

The invention claimed is:

1. A method for the production of methionine, its precursors or derivatives S-acyl methionine (SAM) and N-acyl methionine (NAM) in a fermentative process comprising:
culturing a modified microorganism, overexpressing homoserine succinyltransferase alleles with reduced feedback sensitivity to S-acyl methionine (SAM) and methionine, in an appropriate culture medium comprising a source of carbon, a source of sulphur and a source of nitrogen, and
recovering methionine, and/or its said precursors or derivatives, from said culture medium,
wherein said microorganism is modified by mutating its serine deaminase (sdaA) gene sequence in position 158 with a G nucleotide compared to the wild-type sdaA gene from *E. coli* (SEQ ID NO: 21), thereby increasing serine availability in the microorganism.

2. The method of claim 1, wherein the production of glycine from threonine is reduced.

3. The method of claim 2, wherein the activity of enzymes that convert threonine to glycine is reduced.

4. The method of claim 3, wherein the expression of at least one of the following genes is attenuated: threonine aldolase (ItaE), 2-amino 3-keto butyrate-coA-lyase (kbl), threonine aldolase (glyA), or threonine dehydrogenase (tdh).

5. The method of claim 4, wherein a mutant GlyA enzyme is expressed that has an attenuated threonine aldolase activity, while the serine hydroxymethyl transferase activity of said enzyme GlyA is maintained.

6. The method of claim 5, wherein said mutant GlyA enzyme has at least one of the following amino acid mutations in its polypeptide sequence: 128S, 224S, 225S, 226S, 227S, 230S, or 235K, compared to the wild-type GlyA *E. coli* enzyme (SEQ ID NO: 22).

7. The method according to claim 4, wherein the endogenous gene glyA has been deleted from said microorganism.

8. The method of claim 1, wherein said microorganism is modified in a way that the production of isoleucine from threonine is reduced.

9. The method of claim 8, wherein the deamination and/or the dehydratation of threonine to alpha-ketobutyrate is reduced.

10. The method of claim 9, wherein at least one of the following enzyme activities is attenuated: threonine deaminase, or threonine dehydratase.

11. The method of claim 10, wherein the expression of at least one of the following genes is attenuated: threonine deaminase (ilvA), threonine dehydratase (tdcB), serine deaminase (sdaB), or threonine deaminase (tdcG).

12. The method of claim 1, wherein serine production is increased in said microorganism, by increasing the expression of at least one of the genes phosphoglycerate dehydrogenase (serA), phosphoserine phosphatase (serB), or phosphoserine aminotransferase (serC).

13. The method of claim 1, wherein serine degradation is decreased by attenuating the activity of at least the sdaB gene, encoding enzyme with serine deaminase activity.

14. The method according to claim 1, wherein at least one of the following modification is present in said microorganism:
producing glycine from threonine is reduced;
producing isoleucine from threonine is reduced;
and combinations thereof.

15. The method of claim 1, wherein said modified microorganism is cultured in such conditions that said microorganism is limited or starved for an inorganic substrate.

* * * * *